(12) United States Patent  
Heo

(10) Patent No.: US 11,191,439 B2  
(45) Date of Patent: Dec. 7, 2021

(54) ELECTRONIC DEVICE AND METHOD FOR CAPTURING CONTENTS

(71) Applicant: Samsung Electronics Co., Ltd., Gyeonggi-do (KR)

(72) Inventor: Jun Seok Heo, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 232 days.

(21) Appl. No.: 15/912,650

(22) Filed: Mar. 6, 2018

(65) Prior Publication Data

US 2018/0271388 A1 Sep. 27, 2018

(30) Foreign Application Priority Data

Mar. 24, 2017 (KR) .................. 10-2017-0037962

(51) Int. Cl.
*A61B 5/024* (2006.01)
*A61B 5/00* (2006.01)
(Continued)

(52) U.S. Cl.
CPC .......... *A61B 5/02405* (2013.01); *A61B 5/002* (2013.01); *A61B 5/165* (2013.01);
(Continued)

(58) Field of Classification Search
CPC ....... H04N 21/42201; H04N 21/44218; H04N 21/4756; H04N 21/4755; H04N 21/42661; H04N 21/4335; H04N 21/4126; H04N 21/4135; A61B 5/0002; A61B 5/024; A61B 5/486; A61B 5/02405; A61B 5/6898; A61B 7/7257; A61B 5/002; A61B 5/165; A61B 5/7257; A61B 5/7282; G06F 16/436
See application file for complete search history.

(56) References Cited

U.S. PATENT DOCUMENTS 8,700,009 B2 4/2014 Quy
8,909,022 B1 12/2014 Kasten et al.
(Continued)

FOREIGN PATENT DOCUMENTS

CN 101198277 A 6/2008
CN 104580972 A 4/2015
(Continued)

OTHER PUBLICATIONS

Gaetano Valenza, et al.; "Revealing Real-Time Emotional Responses: a Personalized Assessment based on Heartbeat Dynamics"; Published May 21, 2014; 13 pages; www.nature.com/scientificreports.
(Continued)

*Primary Examiner* — Ngoc K Vu
(74) *Attorney, Agent, or Firm* — Cha & Reiter, LLC

(57) ABSTRACT

Disclosed is an electronic device. The electronic device according to an embodiment includes a memory and a processor electrically connected with the memory, wherein the processor is configured to obtain an identification of a portion of the media data and a sequence of heart rate (HR) data of a user of the electronic device while the portion of media data is output, and store, in the memory, the identification of the portion of the media data when the HR data sequence satisfies a specified condition.

12 Claims, 12 Drawing Sheets

(51) Int. Cl.
*A61B 5/16* (2006.01)
*G06F 16/435* (2019.01)
*G16H 40/60* (2018.01)

(52) U.S. Cl.
CPC .......... *A61B 5/6898* (2013.01); *A61B 5/7257* (2013.01); *A61B 5/7282* (2013.01); *G06F 16/436* (2019.01); *A61B 2503/12* (2013.01); *G16H 40/60* (2018.01)

(56) References Cited

U.S. PATENT DOCUMENTS

| | | | |
|---|---|---|---|
| 9,392,324 B1* | 7/2016 | Maltar | ............... H04N 21/8456 |
| 9,516,259 B2 | 12/2016 | Zheng | |
| 9,866,903 B2 | 1/2018 | Zheng | |
| 9,874,862 B2 | 1/2018 | Lee et al. | |
| 10,623,813 B2 | 4/2020 | Zheng | |
| 2008/0214903 A1 | 9/2008 | Orbach | |
| 2009/0192961 A1* | 7/2009 | Fithian | ..................... G06N 5/04 706/46 |
| 2011/0300847 A1 | 12/2011 | Quy | |
| 2015/0099987 A1 | 4/2015 | Bhatkar et al. | |
| 2015/0297109 A1 | 10/2015 | Garten et al. | |
| 2015/0342479 A1* | 12/2015 | Liu | ..................... A61B 5/02416 600/479 |
| 2016/0371372 A1 | 12/2016 | Chong et al. | |
| 2017/0007165 A1 | 1/2017 | Jain et al. | |
| 2017/0111690 A1* | 4/2017 | Greene | ............ H04N 21/47217 |
| 2017/0178692 A1* | 6/2017 | Wouhaybi | .............. G11B 27/34 |

FOREIGN PATENT DOCUMENTS

| | | |
|---|---|---|
| CN | 105829995 A | 8/2016 |
| JP | 2003-178078 A | 6/2003 |
| KR | 10-2012-0040429 A | 4/2012 |
| KR | 10-2015-0110053 A | 10/2015 |
| KR | 10-2016-0029375 A | 3/2016 |

OTHER PUBLICATIONS

Vladimir Shusterman and Ofer Barnea; "Sympathetic Nervous System Activity in Stress and Biofeedback Relaxation"; IEEE Engineering in Medicine and Bilolgy Magazine; pp. 52-57; Mar./Apr. 2005.
Rui Ding et al.; "YADING: Fast Clustering of Large-Scale Time Series Data"; Microsoft Research; Proceedings of the VLDB Endowment, vol. 8, No. 5; 12 pages.
Liu; "Biosignal controlled recommendation in entertainment systems"; 2010; Printservice Technische Universiteit Eindhoven; ISBN 978-90-386-2402-0.
European Search Report dated May 7, 2018.
Soleymani; "Implicit and Automated Emotional Tagging of Videos"; Nov. 29, 2011; XP055297859; http://cvml.unige.ch/publications/postscript/2011/Soleymani_thesis_2011.pdf.
European Search Report dated Nov. 19, 2019.
Chinese Search Report dated Nov. 24, 2020.
Nirjon et al.; "MusicalHeart: A Hearty Way of Listening to Music"; SenSys '12; Nov. 6-9, 2012; Toronto, ON, Canada.
European Summons to Oral Proceedings dated Jun. 4, 2021.
Chinese Search Report dated Jul. 12, 2021.
Korean Search Report dated Oct. 12, 2021.

* cited by examiner

ELECTRONIC DEVICE AND METHOD FOR CAPTURING CONTENTS

CROSS-REFERENCE TO RELATED APPLICATION(S)

This application claims the benefit under 35 U.S.C. § 119(a) of a Korean patent application filed on Mar. 24, 2017 in the Korean Intellectual Property Office and assigned Serial number 10-2017-0037962, the entire disclosure of which is hereby incorporated by reference.

TECHNICAL FIELD

This disclosure relates to technology for capturing contents output on an electronic device.

DESCRIPTION OF RELATED ART

In recent years, electronic devices, such as smartphones, tablet PCs, wearable devices, and the like, have included a variety of functions. These electronic devices may output various types of contents, such as, a photo, a video, a sound source, a web page, or the like. The electronic devices may capture a section of the contents according to an operation of a user of the electronic devices.

SUMMARY

An electronic device may capture a user-desired section of contents and may insert a tag into the captured section of the contents. However, to capture the user-desired section, the user of the electronic device has to stop the use of the contents and then select the section to be captured, or has to search for the desired section after the use of the contents is completed. Furthermore, to insert the tag into the captured section of the contents, the user of the electronic device has to input the tag to the captured section of the contents.

Aspects of the present disclosure are to address at least the above-mentioned problems and/or disadvantages and to provide at least the advantages described below. Accordingly, an aspect of the present disclosure is to provide an electronic device and a method for automatically capturing a portion of contents based on emotion of a user of the electronic device that is recognized while the contents are being output.

In accordance with an aspect of the present disclosure, an electronic device comprises a memory; and a processor electrically connected with the memory, wherein the processor is configured to: obtain data associated with a portion of the media data and a sequence of heart rate (HR) data of a user of the electronic device that corresponds to the portion of media data while the media data is output; and store, in the memory, the portion of the media data that corresponds to the HR data sequence when the HR data sequence satisfies a specified condition.

In accordance with another aspect of the present disclosure, a method for extracting a portion of media data in an electronic device includes outputting the media data; obtaining data associated with a portion of the media data and a sequence of HR data that corresponds to the portion of the media data, while the media data is output; and storing the portion of media data which corresponds to the HR data sequence when the HR data sequence satisfies a specified condition.

In accordance with another aspect of the present disclosure, an electronic device includes a housing, a display exposed through a portion of the housing, a speaker exposed through a portion of the housing, a communication circuit included in the housing, a processor electrically connected with the display, the speaker, and the communication circuit, and at least one memory electrically connected with the processor. The at least one memory stores instructions that, when executed by the processor, cause the processor to wirelessly connect the electronic device to an external device including an HR sensor using the communication circuit, to play media data stored in the memory, or streamed through the communication circuit, using at least one of the display or the speaker while the electronic device is wirelessly connected with the external device, to receive at least a part of HR data obtained by the HR sensor, through the communication circuit while outputting the media data, store, in the memory, information about the at least a part of the HR data that corresponds to played sections of the media data, and to transmit the stored information to a server through the communication circuit.

According to embodiments of the present disclosure, by determining emotion of a user of an electronic device based on HR data, it is possible to automatically store a partial sequence of contents that causes a change in the emotion of the user of the electronic device.

In addition, the present disclosure may provide various effects that are directly or indirectly recognized.

Other aspects, advantages, and salient features of the disclosure will become apparent to those skilled in the art from the following detailed description, which, taken in conjunction with the annexed drawings, discloses various embodiments of the present disclosure.

BRIEF DESCRIPTION OF THE DRAWINGS

The above and other aspects, features, and advantages of certain embodiments of the present disclosure will be more apparent from the following description taken in conjunction with the accompanying drawings, in which.

Throughout the drawings, it should be noted that like reference numbers are used to depict the same or similar elements, features, and structures.

DETAILED DESCRIPTION

Figure 1:
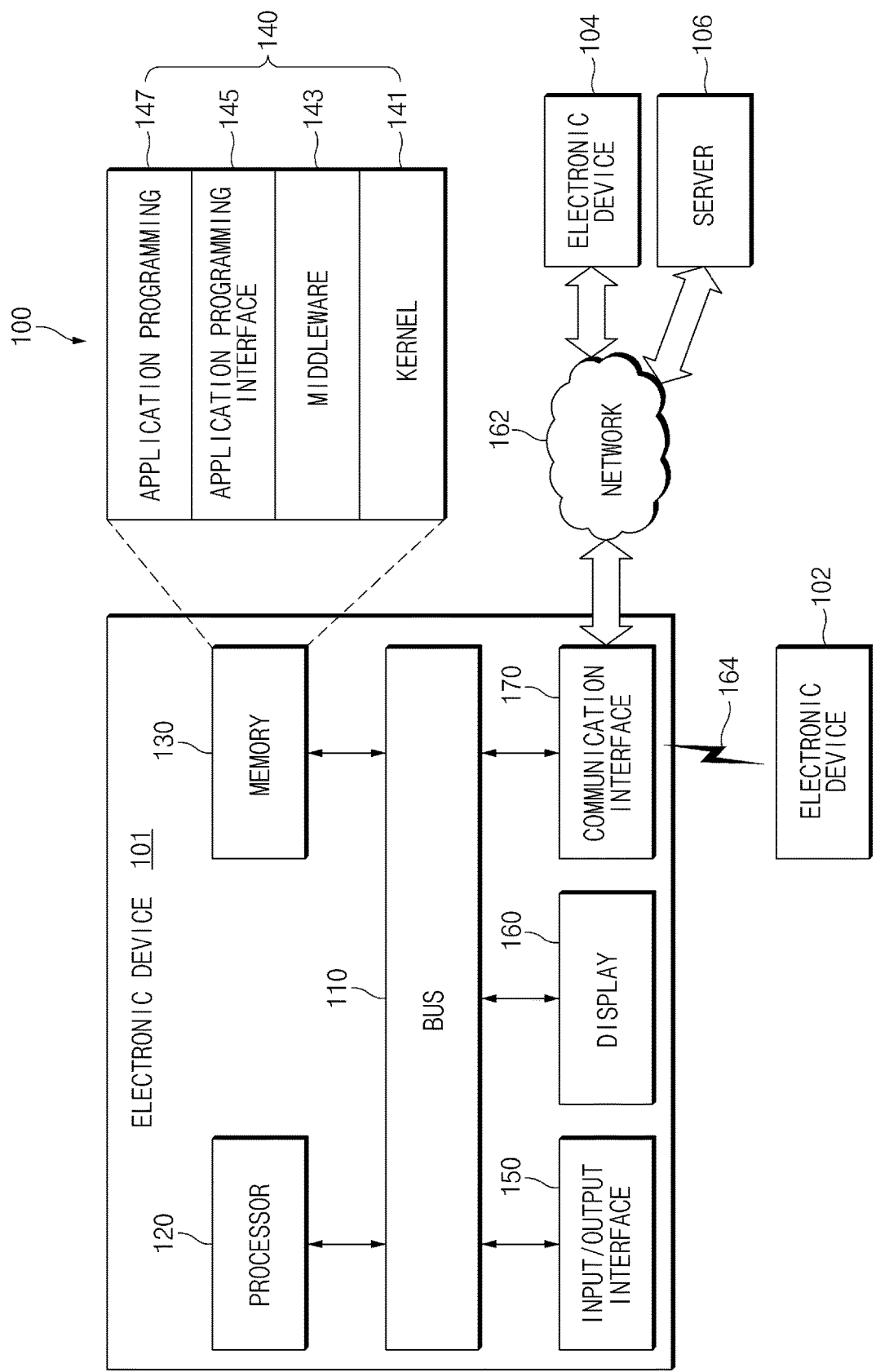
FIG. 1 illustrates an electronic device in a network environment according to various embodiments.

Hereinafter, various embodiments of the present disclosure may be described with reference to accompanying drawings. Accordingly, those of ordinary skill in the art will recognize that modification, equivalent, and/or alternative on the various embodiments described herein can be variously made without departing from the scope and spirit of the present disclosure. With regard to description of drawings, similar elements may be marked by similar reference numerals. The terms of a singular form may include plural forms unless otherwise specified. In this disclosure, the expressions "A or B", "at least one of A or/and B", or "one or more of A or/and B", and the like may include any and all combinations of one or more of the associated listed items. The terms, such as "first", "second", and the like may be used to refer to various elements regardless of the order and/or the priority and to distinguish the relevant elements from other elements, but do not limit the elements. When an element (e.g., a first element) is referred to as being "(operatively or communicatively) coupled with/to" or "connected to" another element (e.g., a second element), the element may be directly coupled with/to or connected to the other element or an intervening element (e.g., a third element) may be present.

According to the situation, the expression "configured to" used in this disclosure may be used as, for example, the expression "suitable for", "having the capacity to", "adapted to", "made to", "capable of", or "designed to" in hardware or software. The expression "a device configured to" may mean that the device is "capable of" operating together with another device or other components. For example, a "processor configured to (or set to) perform A, B, and C" may mean a dedicated processor (e.g., an embedded processor) for performing a corresponding operation or a generic-purpose processor (e.g., a central processing unit (CPU) or an application processor) which performs corresponding operations by executing one or more software programs which are stored in a memory device.

The term "media data" shall be understood to mean a collection of serially ordered data. For example, media data can include a picture, wherein the pixels of the picture are spatially ordered. Media data can include video data, wherein video frames are ordered by time. Media data can include audio data, wherein the audio data can include digitized amplitudes of signal(s) that are ordered in time. Media data can include a document, where data is ordered by pages. It is noted that in some cases, the media data can be stored as a file on the device outputting the media. Alternatively, the media data can be streamed to the device from another device that stores the media data as a file.

Users can have differing emotional reactions when reading, watching, or listening to various media data. For example, a user might feel sadness when watching a particular movie scene. Alternatively, a user might get angry when reading an article about a particular political event. As another alternative, a user may feel inspired when listening to the chorus of a particular song.

Certain embodiments of this disclosure capture the user's emotional reactions when reading, watching and listening to portions of various output media data. An electronic device (as will be described in FIGS. 1-3) typically outputs the media data. The output can include, for example, a display or a speaker. According to certain embodiments, an external electronic device (described in FIG. 4, 41, FIG. 5, 51) can measure biological data of the user, such as their heart rate, while reading, watching, or listening to the media data. The external device can send and the electronic device outputting the media data can receive the biological data of the user. Both the biological data and the media data can be associated with a common time base, especially in the case of audio and video data. That is, the biological data and media can be represented as a function of time.

The electronic device can examine and detect whether the biological data indicates a strong emotional reaction. For example, an abrupt change in the biological data, such as a drop in heart rate or increase in heart rate, can be indicative of a strong emotional reaction. When a strong emotional reaction is detected during a window of time, biological data during the window of time and the portion of the media data output during the window of time can be stored. It is noted that the portion of the output media during the window of time may be part of a larger media data file, such as a larger video, audio, or document file. According to an embodiment of this disclosure, the portion of the media during the window time is stored separately from the entire media file. Moreover, in certain embodiments, the storage of the media during the window of time can exclude media outside the window of time.

Electronic Device

An electronic device according to various embodiments of this disclosure may include at least one of, for example, smartphones, tablet personal computers (PCs), mobile phones, video telephones, electronic book readers, desktop PCs, laptop PCs, netbook computers, workstations, servers, personal digital assistants (PDAs), portable multimedia players (PMPs), Motion Picture Experts Group (MPEG-1 or MPEG-2) Audio Layer 3 (MP3) players, medical devices, cameras, or wearable devices. According to various embodiments, the wearable device may include at least one of an accessory type (e.g., watches, rings, bracelets, anklets, necklaces, glasses, contact lens, or head-mounted-devices (HMDs), a fabric or garment-integrated type (e.g., an electronic apparel), a body-attached type (e.g., a skin pad or tattoos), or a bio-implantable type (e.g., an implantable circuit). According to various embodiments, the electronic device may include at least one of, for example, televisions (TVs), digital versatile disc (DVD) players, audios, refrigerators, air conditioners, cleaners, ovens, microwave ovens, washing machines, air cleaners, set-top boxes, home automation control panels, security control panels, media boxes (e.g., Samsung HomeSync™, Apple TV™, or Google TV™), game consoles (e.g., Xbox™ or PlayStation™), electronic dictionaries, electronic keys, camcorders, electronic picture frames, and the like.

According to another embodiment, an electronic device may include at least one of various medical devices (e.g., various portable medical measurement devices (e.g., a blood glucose monitoring device, a heartbeat measuring device, a blood pressure measuring device, a body temperature measuring device, and the like), a magnetic resonance angiography (MRA), a magnetic resonance imaging (MRI), a computed tomography (CT), scanners, and ultrasonic devices), navigation devices, Global Navigation Satellite System (GNSS), event data recorders (EDRs), flight data recorders (FDRs), vehicle infotainment devices, electronic equipment for vessels (e.g., navigation systems and gyrocompasses), avionics, security devices, head units for vehicles, industrial or home robots, drones, automatic teller's machines (ATMs), points of sales (POSs) of stores, or internet of things (e.g., light bulbs, various sensors, sprinkler devices, fire alarms, thermostats, street lamps, toasters, exercise equipment, hot water tanks, heaters, boilers, and the like). According to an embodiment, the electronic device may include at least one of parts of furniture or buildings/structures, electronic boards, electronic signature receiving devices, projectors, or various measuring instruments (e.g., water meters, electricity meters, gas meters, or wave meters, and the like). According to various embodiments, the electronic device may be a flexible electronic device or a combination of two or more above-described devices. Furthermore, an electronic device according to an embodiment of this disclosure may not be limited to the above-described electronic devices. In this disclosure, the term "user" may refer to a person who uses an electronic device or may refer to a device (e.g., an artificial intelligence electronic device) that uses the electronic device.

Referring to FIG. 1, according to various embodiments, an electronic device 101 in a network environment is described. The electronic device 101 may include a bus 110, a processor 120, a memory 130, an input/output interface 150, a display 160, and a communication interface 170. According to an embodiment, the electronic device 101 may not include at least one of the above-described elements or may further include other element(s). The bus 110 may interconnect the above-described elements 110 to 170 and may include a circuit for conveying communications (e.g., a control message and/or data) among the above-described elements. The processor 120 may include one or more of a central processing unit (CPU), an application processor (AP), or a communication processor (CP). For example, the processor 120 may perform an arithmetic operation or data processing associated with control and/or communication of at least other elements of the electronic device 101.

The memory 130 may include a volatile and/or nonvolatile memory. For example, the memory 130 may store instructions or data associated with at least one other element(s) of the electronic device 101. According to an embodiment, the memory 130 may store software and/or a program 140. The program 140 may include, for example, a kernel 141, a middleware 143, an application programming interface (API) 145, and/or an application program (or "an application") 147. At least a part of the kernel 141, the middleware 143, or the API 145 may be referred to as an "operating system (OS)". For example, the kernel 141 may control or manage system resources (e.g., the bus 110, the processor 120, the memory 130, and the like) that are used to execute operations or functions of other programs (e.g., the middleware 143, the API 145, and the application program 147). Furthermore, the kernel 141 may provide an interface that allows the middleware 143, the API 145, or the application program 147 to access discrete elements of the electronic device 101 so as to control or manage system resources.

The middleware 143 may perform, for example, a mediation role such that the API 145 or the application program 147 communicates with the kernel 141 to exchange data. Furthermore, the middleware 143 may process one or more task requests received from the application program 147 according to a priority. For example, the middleware 143 may assign the priority, which makes it possible to use a system resource (e.g., the bus 110, the processor 120, the memory 130, or the like) of the electronic device 101, to at least one of the application program 147 and may process the one or more task requests. The API 145 may be an interface through which the application program 147 controls a function provided by the kernel 141 or the middleware 143, and may include, for example, at least one interface or function (e.g., a command or an instruction) for a file control, a window control, image processing, a character control, or the like. The input/output interface 150 may transmit an instruction or data input from a user or another external device, to other element(s) of the electronic device 101 or may output an instruction or data, received from other element(s) of the electronic device 101, to a user or another external device.

The display 160 may include, for example, a liquid crystal display (LCD), a light-emitting diode (LED) display, an organic LED (OLED) display, a microelectromechanical systems (MEMS) display, or an electronic paper display. The display 160 may display, for example, various contents (e.g., a text, an image, a video, an icon, a symbol, and the like) to a user. The display 160 may include a touch screen and may receive, for example, a touch, gesture, proximity, or hovering input using an electronic pen or a part of a user's body. For example, the communication interface 170 may establish communication between the electronic device 101 and an external device (e.g., the first electronic device 102, the second electronic device 104, or the server 106). For example, the communication interface 170 may be connected to the network 162 over wireless communication or wired communication to communicate with the external device (e.g., the second electronic device 104 or the server 106).

For example, the wireless communication may include cellular communication using at least one of long-term evolution (LTE), LTE Advanced (LTE-A), Code Division Multiple Access (CDMA), Wideband CDMA (WCDMA), Universal Mobile Telecommunications System (UMTS), Wireless Broadband (WiBro), Global System for Mobile Communications (GSM), or the like. The wireless communication may include at least one of wireless fidelity (Wi-Fi), Bluetooth, Bluetooth low energy (BLE), Zigbee, near field communication (NFC), magnetic stripe transmission (MST), radio frequency (RF), a body area network, or the like. According to an embodiment, the wireless communication may include GNSS. The GNSS may be one of, for example, a global positioning system (GPS), a global navigation satellite system (Glonass), a Beidou navigation satellite system (hereinafter referred to as "Beidou"), or an European global satellite-based navigation system (hereinafter referred to as "Galileo"). Hereinafter, in this disclosure, "GPS" and "GNSS" may be interchangeably used. The wired communication may include at least one of, for example, a universal serial bus (USB), a high definition multimedia interface (HDMI), a recommended standard-232 (RS-232), power line communication, a plain old telephone service (POTS), or the like. The network 162 may include at least one of telecommunications networks, for example, a computer network (e.g., LAN or WAN), an Internet, or a telephone network.

Each of the first and second external electronic devices 102 and 104 may be a device of which the type is different from or the same as that of the electronic device 101. According to various embodiments, all or a portion of operations that the electronic device 101 will perform may be executed by another or plural electronic devices (e.g., the first electronic device 102, the second electronic device 104 or the server 106). According to an embodiment, in the case where the electronic device 101 executes any function or service automatically or in response to a request, the electronic device 101 may not perform the function or the service internally, but, alternatively additionally, it may request at least a portion of a function associated with the electronic device 101 at other electronic device (e.g., the electronic device 102 or 104 or the server 106). The other electronic device (e.g., the electronic device 102 or 104 or the server 106) may execute the requested function or additional function and may transmit the execution result to the electronic device 101. The electronic device 101 may provide the requested function or service using the received result or may additionally process the received result to provide the requested function or service. To this end, for example, cloud computing, distributed computing, or client-server computing may be used.

According to certain embodiments of the present disclosure, the electronic device 101 can output media data, via for example, the display 160. The communication interface 170 can receive a sequence of heart rate (HR) data of a user viewer watching the display, while outputting the media data. The processor 120 can obtain an identification of a portion of the media data and a sequence of heart rate (HR) data of a user of the electronic device 101 while the portion of the media data is output. The memory can then store the identification of the portion of the media data when the HR data sequence satisfies a specified condition.

Figure 2:
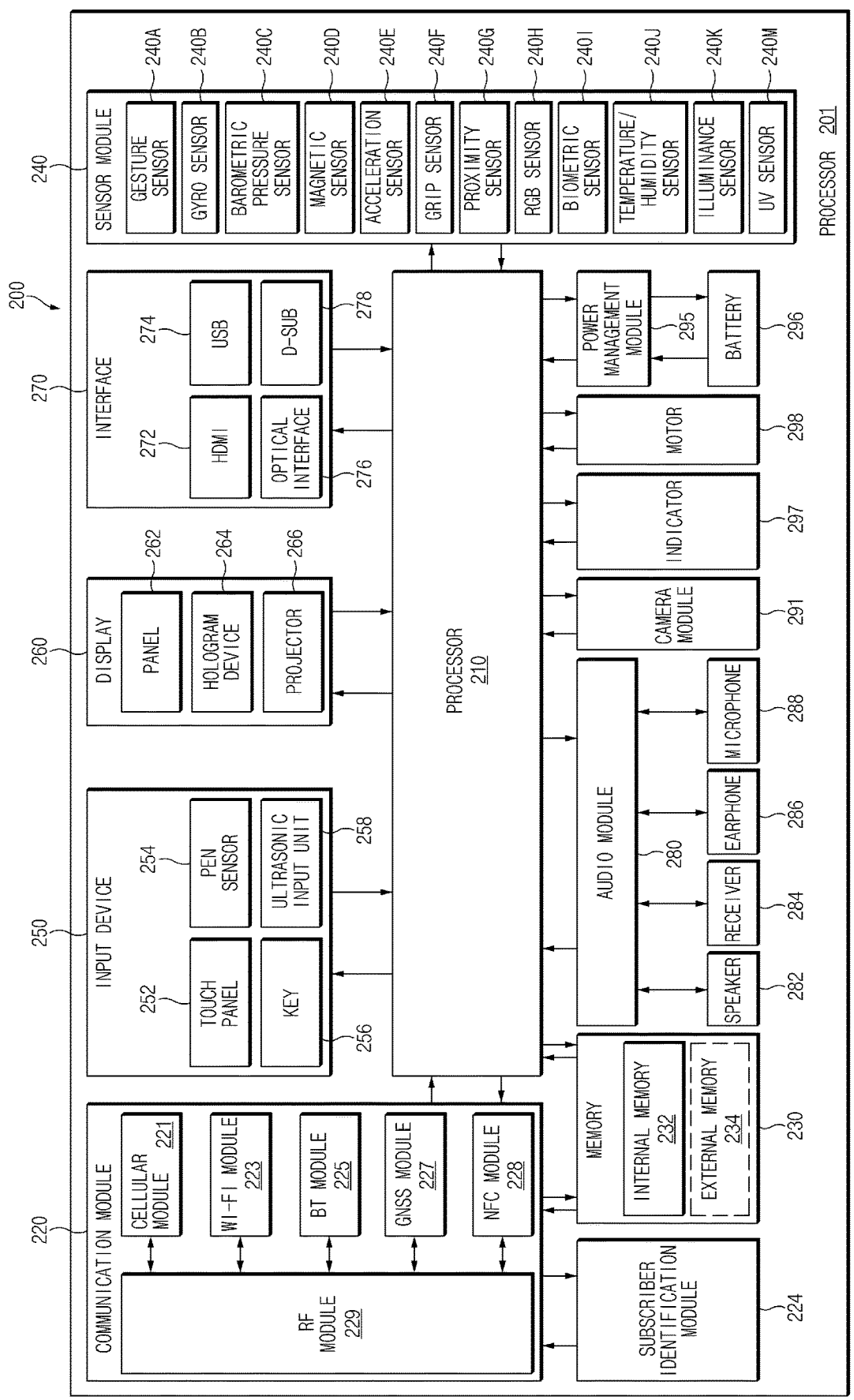
FIG. 2 is a block diagram of an electronic device according to various embodiments.

FIG. 2 illustrates a block diagram of an electronic device, according to various embodiments. An electronic device 201 may include, for example, all or a part of the electronic device 101 illustrated in FIG. 1. The electronic device 201 may include one or more processors (e.g., an application processor (AP)) 210, a communication module 220, a subscriber identification module 224, a memory 230, a sensor module 240, an input device 250, a display 260, an interface 270, an audio module 280, a camera module 291, a power management module 295, a battery 296, an indicator 297, and a motor 298. For example, the processor 210 may be implemented with a System on Chip (SoC). According to an embodiment, the processor 210 may further include a graphic processing unit (GPU) and/or an image signal processor. The processor 210 may include at least a part (e.g., a cellular module 221) of elements illustrated in FIG. 2. The processor 210 may load an instruction or data, which is received from at least one of other elements (e.g., a nonvolatile memory), into a volatile memory and process the loaded instruction or data. The processor 210 may store result data in the nonvolatile memory.

The communication module 220 may be configured the same as or similar to the communication interface 170 of FIG. 1. The communication module 220 may include the cellular module 221, a Wi-Fi module 223, a Bluetooth (BT) module 225, a GNSS module 227, a near field communication (NFC) module 228, and a radio frequency (RF) module 229. The cellular module 221 may provide, for example, voice communication, video communication, a character service, an Internet service, or the like over a communication network. According to an embodiment, the cellular module 221 may perform discrimination and authentication of the electronic device 201 within a communication network by using the subscriber identification module (e.g., a SIM card) 224. According to an embodiment, the cellular module 221 may perform at least a portion of functions that the processor 210 provides. According to an embodiment, the cellular module 221 may include a communication processor (CP). According to an embodiment, at least a part (e.g., two or more) of the cellular module 221, the Wi-Fi module 223, the BT module 225, the GNSS module 227, or the NFC module 228 may be included within one Integrated Circuit (IC) or an IC package. For example, the RF module 229 may transmit and receive a communication signal (e.g., an RF signal). For example, the RF module 229 may include a transceiver, a power amplifier module (PAM), a frequency filter, a low noise amplifier (LNA), an antenna, or the like. According to another embodiment, at least one of the cellular module 221, the Wi-Fi module 223, the BT module 225, the GNSS module 227, or the NFC module 228 may transmit and receive an RF signal through a separate RF module. The subscriber identification module 224 may include, for example, a card and/or embedded SIM that includes a subscriber identification module and may include unique identify information (e.g., integrated circuit card identifier (ICCID)) or subscriber information (e.g., international mobile subscriber identity (IMSI)).

The memory 230 (e.g., the memory 130) may include an internal memory 232 or an external memory 234. For example, the internal memory 232 may include at least one of a volatile memory (e.g., a dynamic random access memory (DRAM), a static RAM (SRAM), a synchronous DRAM (SDRAM), or the like), a nonvolatile memory (e.g., a one-time programmable read only memory (OTPROM), a programmable ROM (PROM), an erasable and programmable ROM (EPROM), an electrically erasable and programmable ROM (EEPROM), a mask ROM, a flash ROM, a flash memory, a hard drive, or a solid state drive (SSD). The external memory 234 may include a flash drive such as compact flash (CF), secure digital (SD), micro secure digital (Micro-SD), mini secure digital (Mini-SD), extreme digital (xD), a multimedia card (MMC), a memory stick, or the like. The external memory 234 may be operatively and/or physically connected to the electronic device 201 through various interfaces.

The sensor module 240 may measure, for example, a physical quantity or may detect an operation state of the electronic device 201. The sensor module 240 may convert the measured or detected information to an electric signal. For example, the sensor module 240 may include at least one of a gesture sensor 240A, a gyro sensor 240B, a barometric pressure sensor 240C, a magnetic sensor 240D, an acceleration sensor 240E, a grip sensor 240F, the proximity sensor 240G, a color sensor 240H (e.g., red, green, blue (RGB) sensor), a biometric sensor 240I, a temperature/humidity sensor 240J, an illuminance sensor 240K, or an UV sensor 240M. Although not illustrated, additionally or generally, the sensor module 240 may further include, for example, an E-nose sensor, an electromyography (EMG) sensor, an electroencephalogram (EEG) sensor, an electrocardiogram (ECG) sensor, an infrared (IR) sensor, an iris sensor, and/or a fingerprint sensor. The sensor module 240 may further include a control circuit for controlling at least one or more sensors included therein. According to an embodiment, the electronic device 201 may further include a processor that is a part of the processor 210 or independent of the processor 210 and is configured to control the sensor module 240. The processor may control the sensor module 240 while the processor 210 remains at a sleep state.

The input device 250 may include, for example, a touch panel 252, a (digital) pen sensor 254, a key 256, or an ultrasonic input unit 258. For example, the touch panel 252 may use at least one of capacitive, resistive, infrared and ultrasonic detecting methods. Also, the touch panel 252 may further include a control circuit. The touch panel 252 may further include a tactile layer to provide a tactile reaction to a user. The (digital) pen sensor 254 may be, for example, a part of a touch panel or may include an additional sheet for recognition. The key 256 may include, for example, a physical button, an optical key, or a keypad. The ultrasonic input device 258 may detect (or sense) an ultrasonic signal, which is generated from an input device, through a microphone (e.g., a microphone 288) and may check data corresponding to the detected ultrasonic signal.

The display 260 (e.g., the display 160) may include a panel 262, a hologram device 264, a projector 266, and/or a control circuit for controlling the panel 262, the hologram device 264, or the projector 266. The panel 262 may be implemented, for example, to be flexible, transparent or wearable. The panel 262 and the touch panel 252 may be integrated into a single module. According to an embodiment, the panel 262 may include a pressure sensor (or force sensor) that measures the intensity of touch pressure by a user. The pressure sensor may be implemented integrally with the touch panel 252, or may be implemented as at least one sensor separately from the touch panel 252. The hologram device 264 may display a stereoscopic image in a space using a light interference phenomenon. The projector 266 may project light onto a screen so as to display an image. For example, the screen may be arranged in the inside or the outside of the electronic device 201. The interface 270 may include, for example, a high-definition multimedia interface (HDMI) 272, a universal serial bus (USB) 274, an optical interface 276, or a D-subminiature (D-sub) 278. The interface 270 may be included, for example, in the communication interface 170 illustrated in FIG. 1. Additionally or generally, the interface 270 may include, for example, a mobile high definition link (MHL) interface, a SD card/multi-media card (MMC) interface, or an infrared data association (IrDA) standard interface.

The audio module 280 may convert a sound and an electric signal in dual directions. At least a part of the audio module 280 may be included, for example, in the input/output interface 150 illustrated in FIG. 1. The audio module 280 may process, for example, sound information that is input or output through a speaker 282, a receiver 284, an earphone 286, or the microphone 288. For example, the camera module 291 may shoot a still image or a video. According to an embodiment, the camera module 291 may include at least one or more image sensors (e.g., a front sensor or a rear sensor), a lens, an image signal processor (ISP), or a flash (e.g., an LED or a xenon lamp). The power management module 295 may manage, for example, power of the electronic device 201. According to an embodiment, a power management integrated circuit (PMIC), a charger IC, or a battery or fuel gauge may be included in the power management module 295. The PMIC may have a wired charging method and/or a wireless charging method. The wireless charging method may include, for example, a magnetic resonance method, a magnetic induction method or an electromagnetic method and may further include an additional circuit, for example, a coil loop, a resonant circuit, a rectifier, or the like. The battery gauge may measure, for example, a remaining capacity of the battery 296 and a voltage, current or temperature thereof while the battery is charged. The battery 296 may include, for example, a rechargeable battery and/or a solar battery.

The indicator 297 may display a specific state of the electronic device 201 or a part thereof (e.g., the processor 210), such as a booting state, a message state, a charging state, and the like. The motor 298 may convert an electrical signal into a mechanical vibration and may generate the following effects: vibration, haptic, and the like. The electronic device 201 may include a processing device (e.g., a GPU) for supporting a mobile TV. The processing device for supporting the mobile TV may process media data according to the standards of digital multimedia broadcasting (DMB), digital video broadcasting (DVB), MediaFLO™, or the like. Each of the above-mentioned elements of the electronic device according to various embodiments of the present disclosure may be configured with one or more components, and the names of the elements may be changed according to the type of the electronic device. In various embodiments, some elements of the electronic device (e.g., the electronic device 201) may be omitted or other additional elements may be added. Furthermore, some of the elements of the electronic device may be combined with each other so as to form one entity, so that the functions of the elements may be performed in the same manner as before the combination.

According to certain embodiments of the present disclosure, the electronic device 200 can output media data, via for example, the display 260, speaker 282, or earphone 286. In one embodiment, the biometric sensor 240L can measure and provide a sequence of heart rate (HR) data of a user viewing the display or listening to the speaker 282 or earphone 286. In another embodiment, communication module 220 can receive a sequence of heart rate (HR) data of a user viewer watching the display, or listening to the speaker 282/earphone 286 while outputting the media data. The processor 120 can obtain an identification of a portion of the media data and a sequence of heart rate (HR) data of a user of the electronic device 200 while the portion of the media data is output. The memory can then store the identification of the portion of the media data when the HR data sequence satisfies a specified condition.

Figure 3:
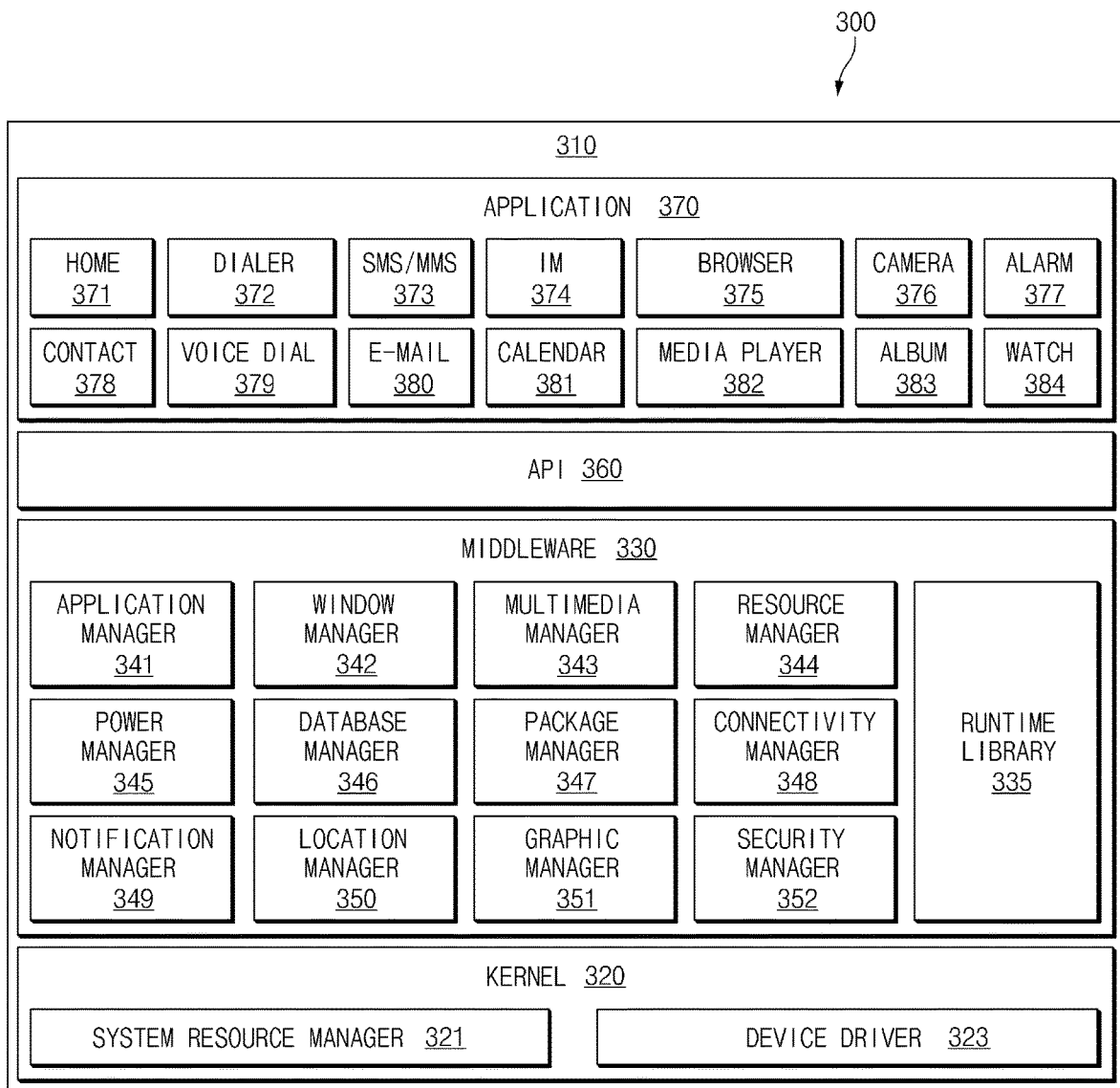
FIG. 3 is a block diagram of a program module according to various embodiments.

FIG. 3 illustrates a block diagram of a program module, according to various embodiments. According to an embodiment, a program module 310 (e.g., the program 140) may include an operating system (OS) to control resources associated with an electronic device (e.g., the electronic device 101), and/or diverse applications (e.g., the application program 147) driven on the OS. The OS may be, for example, Android™, iOS™, Windows™, Symbian™, Tizen™, or Bada™. The program module 310 may include a kernel 320 (e.g., the kernel 141), a middleware 330 (e.g., the middleware 143), an application programming interface (API) 360 (e.g., the API 145), and/or an application 370 (e.g., the application program 147). At least a portion of the program module 310 may be preloaded on an electronic device or may be downloadable from an external electronic device (e.g., the first electronic device 102, the second electronic device 104, the server 106, or the like).

The kernel 320 (e.g., the kernel 141) may include, for example, a system resource manager 321 or a device driver 323. The system resource manager 321 may control, allocate, or retrieve system resources. According to an embodiment, the system resource manager 321 may include a process managing unit, a memory managing unit, a file system managing unit, or the like. The device driver 323 may include, for example, a display driver, a camera driver, a Bluetooth driver, a shared memory driver, a USB driver, a keypad driver, a Wi-Fi driver, an audio driver, or an inter-process communication (IPC) driver. The middleware 330 may provide, for example, a function that the application 370 needs in common, or may provide diverse functions to the application 370 through the API 360 to allow the application 370 to efficiently use limited system resources of the electronic device. According to an embodiment, the middleware 330 may include at least one of a runtime library 335, an application manager 341, a window manager 342, a multimedia manager 343, a resource manager 344, a power manager 345, a database manager 346, a package manager 347, a connectivity manager 348, a notification manager 349, a location manager 350, a graphic manager 351, or a security manager 352.

The runtime library 335 may include, for example, a library module that is used by a compiler to add a new function through a programming language while the application 370 is being executed. The runtime library 335 may perform input/output management, memory management, or capacities about arithmetic functions. The application manager 341 may manage, for example, a life cycle of at least one application of the application 370. The window manager 342 may manage a graphic user interface (GUI) resource that is used in a screen. The multimedia manager 343 may identify a format necessary for playing diverse media files, and may perform encoding or decoding of media files by using a codec suitable for the format. The resource manager 344 may manage resources such as a memory space or source code of the application 370. The power manager 345 may manage a battery or power, and may provide power information for an operation of an electronic device. According to an embodiment, the power manager 345 may operate with a basic input/output system (BIOS). The database manager 346 may generate, search for, or modify database that is to be used in the application 370. The package manager 347 may install or update an application that is distributed in the form of package file.

The connectivity manager 348 may manage, for example, wireless connection. The notification manager 349 may provide an event, for example, arrival message, appointment, or proximity notification to a user. For example, the location manager 350 may manage location information about an electronic device. The graphic manager 351 may manage a graphic effect that is provided to a user, or manage a user interface relevant thereto. The security manager 352 may provide, for example, system security or user authentication. According to an embodiment, the middleware 330 may include a telephony manager for managing a voice or video call function of the electronic device or a middleware module that combines diverse functions of the above-described elements. According to an embodiment, the middleware 330 may provide a module specialized to each OS kind to provide differentiated functions. Additionally, the middleware 330 may dynamically remove a part of the preexisting elements or may add new elements thereto. The API 360 may be, for example, a set of programming functions and may be provided with a configuration that is variable depending on an OS. For example, in the case where an OS is the android or the iOS, it may provide one API set per platform. In the case where an OS is the tizen, it may provide two or more API sets per platform.

The application 370 may include, for example, applications such as a home 371, a dialer 372, an SMS/MMS 373, an instant message (IM) 374, a browser 375, a camera 376, an alarm 377, a contact 378, a voice dial 379, an e-mail 380, a calendar 381, a media player 382, an album 383, a watch 384, health care (e.g., measuring an exercise quantity, blood sugar, or the like) or offering of environment information (e.g., information of barometric pressure, humidity, temperature, or the like). According to an embodiment, the application 370 may include an information exchanging application to support information exchange between an electronic device and an external electronic device. The information exchanging application may include, for example, a notification relay application for transmitting specific information to an external electronic device, or a device management application for managing the external electronic device. For example, the notification relay application may include a function of transmitting notification information, which arise from other applications, to an external electronic device or may receive, for example, notification information from an external electronic device and provide the notification information to a user. The device management application may install, delete, or update for example, a function (e.g., turn-on/turn-off of an external electronic device itself (or a part of components) or adjustment of brightness (or resolution) of a display) of the external electronic device which communicates with the electronic device, and an application running in the external electronic device. According to an embodiment, the application 370 may include an application (e.g., a health care application of a mobile medical device) that is assigned in accordance with an attribute of an external electronic device. According to an embodiment, the application 370 may include an application that is received from an external electronic device. At least a portion of the program module 310 may be implemented by software, firmware, hardware (e.g., the processor 210), or a combination (e.g., execution) of two or more thereof, and may include modules, programs, routines, sets of instructions, processes, or the like for performing one or more functions.

In certain embodiments, browser 375, media player 382, can cause the display 260, speaker 282, or microphone 286 to output media data.

Figure 4:
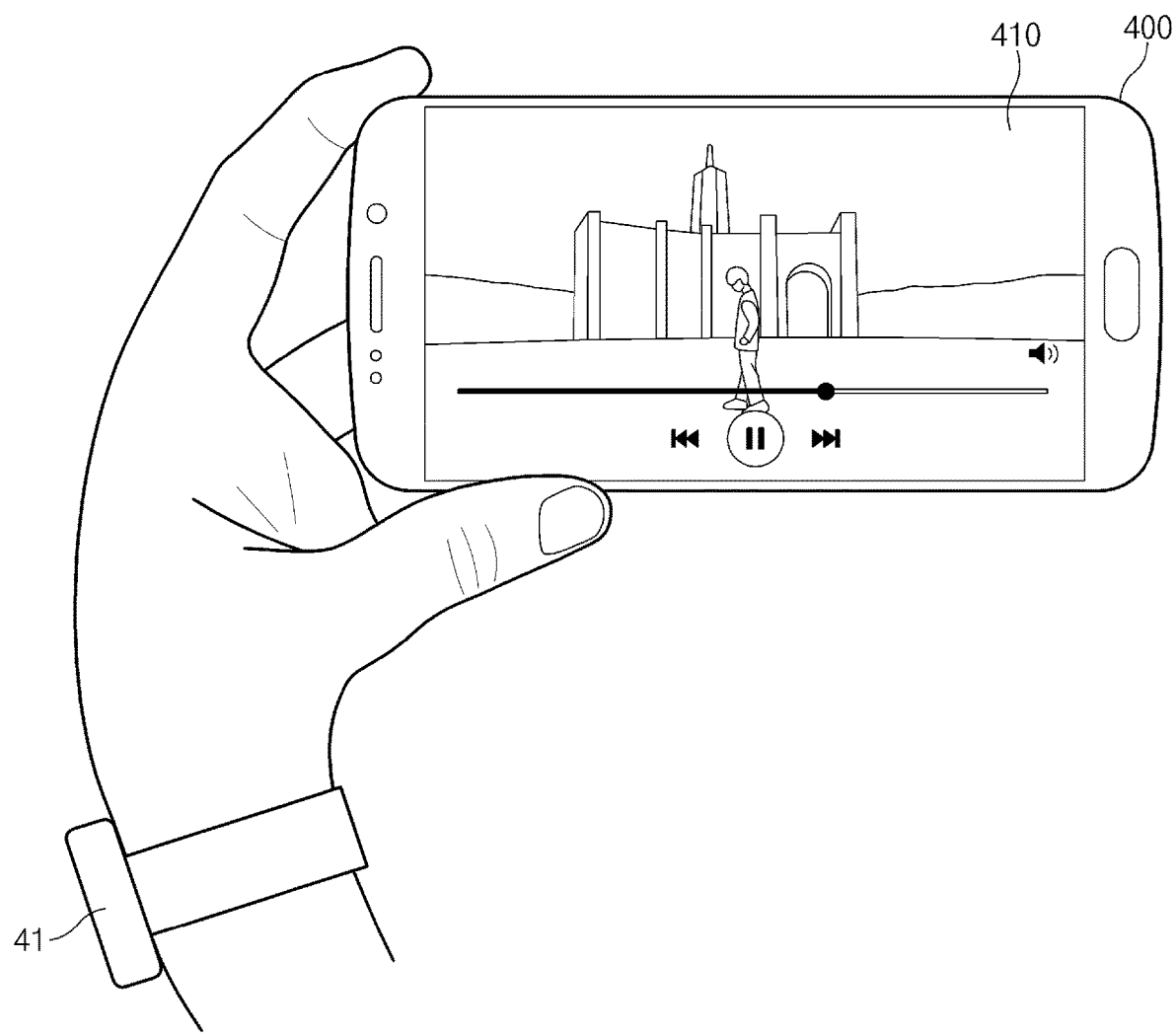
FIG. 4 illustrates an operating environment of an electronic device, according to an embodiment.

FIG. 4 illustrates an operating environment of an electronic device, according to an embodiment.

Referring to FIG. 4, an electronic device 400 according to an embodiment may output media data 410. For example, the output media data 410 can include reproduced, or played back content. A user of the electronic device 400 may use an external device 41, such as a smartwatch, along with the electronic device 400. The electronic device 400 may operate in conjunction with the external device 41. The electronic device 400 may obtain heart rate (HR) data of the user of the electronic device 400 from the external device 41 or the electronic device 400 while the media data 410 is output. The electronic device 400 may obtain an HR data sequence that contains continuous HR data. The electronic device 400 may perform a frequency analysis on the HR data sequence to determine a change in emotion of the user of the electronic device 400. The electronic device 400 may obtain a portion of the media data or an identification of the portion of the media data 410 that corresponds to the period of time during which the change in the user's emotion has been detected. The electronic device 400 may store the portion of the media data or the identification of the media data 410. The electronic device 400 may infer the user's emotion and may tag the portion of the media data 410 with the inferred emotion. As described above, the electronic device 400 according to an embodiment may automatically capture the portion of the media data 410, which is associated with the change in the emotion of the user of the electronic device 400, based on the HR data. A specific structure and operation of an electronic device according to an embodiment will be described below in detail with reference to FIG. 5.

Figure 5:
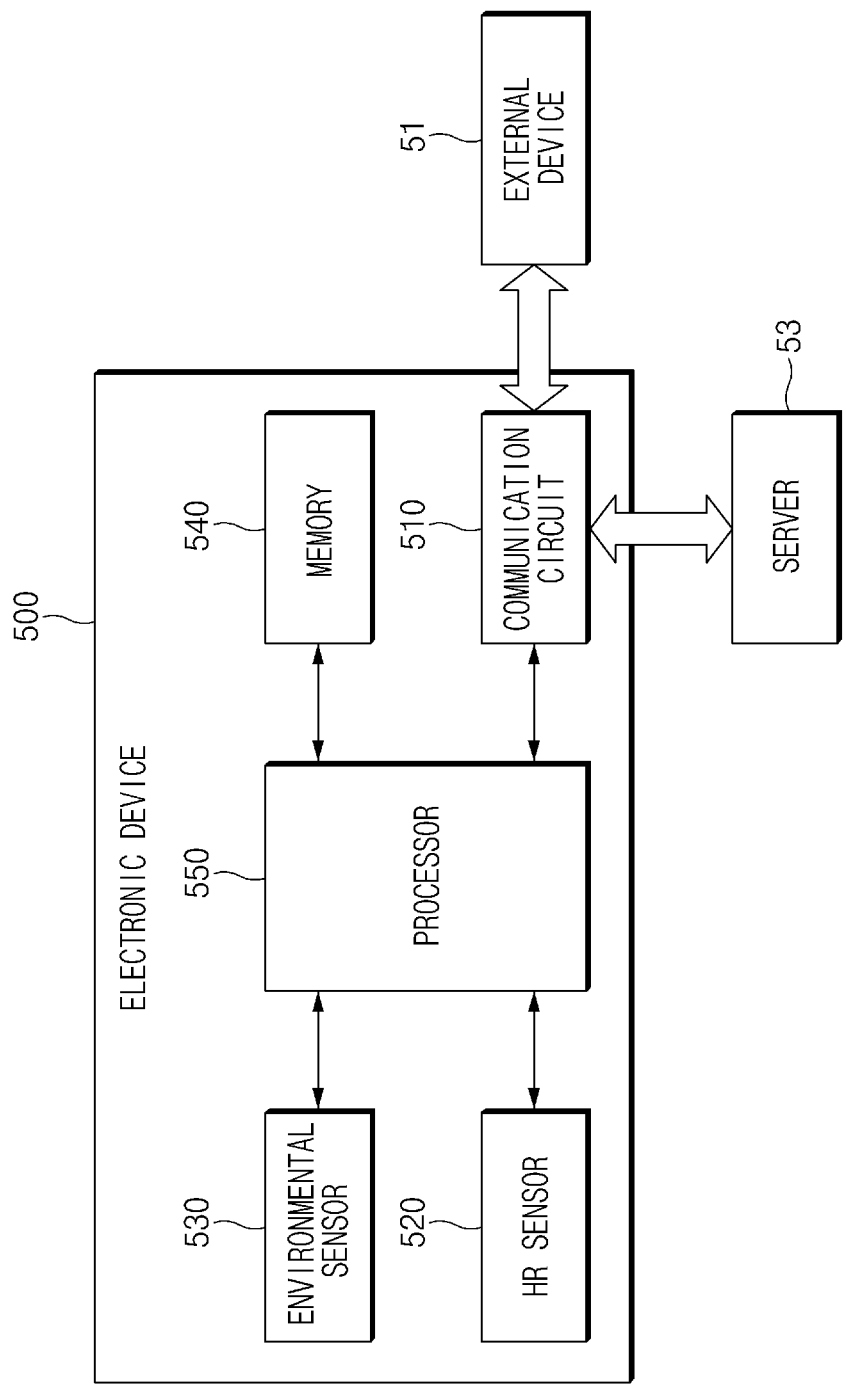
FIG. 5 is a block diagram illustrating a configuration of an electronic device according to an embodiment.

FIG. 5 is a block diagram illustrating a configuration of an electronic device according to an embodiment.

Referring to FIG. 5, an electronic device 500 according to an embodiment may include a communication circuit 510, an HR sensor 520, an environmental sensor 530, a memory 540, and a processor 550. The electronic device 500 may also be referred to as a mobile device, a mobile terminal, user equipment (UE), or the like.

An external device 51 according to an embodiment may obtain a user's HR data. The external device 51 may be, for example, a wearable device that also includes an HR sensor 520.

A server 53 according to an embodiment may be a computing device that receives data from the electronic device 500 and processes and stores the received data. According to an embodiment, the server 53 may provide media data to the electronic device 500. For example, the server 53 may store various types of media data and may share or recommend some of the media data.

The communication circuit 510 according to an embodiment may communicate with the external device 51 and/or the server 53. For example, the communication circuit 510 may communicate with the external device 51 by using a communication method, such as Bluetooth, Bluetooth low energy (BLE), Wi-Fi Direct, or the like. In another example, the communication circuit 510 may communicate with the server 53 by using a communication method, such as long term evolution (LTE), Wi-Fi, or the like. Without being limited thereto, the communication circuit 510 may include one or more of various types of modules that support communication with the external device 51 and/or the server 53.

The HR sensor 520 according to an embodiment may sense an HR of a user of the electronic device 500. The HR sensor 520 may obtain HR data of the user of the electronic device 500. The electronic device 500 may obtain HR data by using the HR sensor 520 and may obtain HR data from the external device 51 by using the communication circuit 510.

The environmental sensor 530 according to an embodiment may obtain environmental information of the electronic device 500. The environmental sensor 530 may include at least some of various elements, such as a microphone, a camera, a gyro sensor, an illuminance sensor, a GPS module, or the like. The environmental information may include information about, for example, sound, image, acceleration, angular velocity, illuminance, and/or position obtained by the environmental sensor 530. The environmental information may include information about a running application in the electronic device 500 and/or information about the external device 51 connected with the electronic device 500.

The memory 540 according to an embodiment may temporarily or non-temporarily store various pieces of data and information. For example, the memory 540 may store media data, a portion of the media data, HR data of the user of the electronic device 500, an HR data sequence, environmental information, and/or emotional information. The portion of the media data can exclude the remainder of the media data.

The processor 550 according to an embodiment may be electrically connected with the communication circuit 510, the HR sensor 520, the environmental sensor 530, and the memory 540. The processor 550 may control the communication circuit 510, the HR sensor 520, the environmental sensor 530, and the memory 540.

According to an embodiment, the processor 550 may output (or play back) contents. The processor 550 may output various media data, such as a photo, a photo slideshow, video data, audio data, and/or a web page. The processor 550 may play back the media data, with the external device 51 being connected thereto. The processor 550 may play back the media data stored in the memory 540 or media data streamed through the communication circuit 510, by using at least one of, for example, the display module 260 or the speaker 282/microphone 286 of FIG. 2.

The processor 550 may also output the media data by using various types of output devices other than the display module 260 or the speaker 282 of FIG. 2.

According to an embodiment, while the media data is output, the processor 550 may obtain an identification of a portion of the media data and a sequence of heart rate (HR) data of a user of the electronic device 500 that corresponds to the portion of the media data. The processor 550 may capture and store the portion of the media data in the memory 540 while the media data is output. For example, the processor 550 may sequentially capture portions of the media data by using a sliding window. The processor 550 may obtain time data corresponding to the portion of the media data while the media data is output. The time data may be, for example, data that represents the period of time during which the portion of the media data has been played back. For example, the processor 550 may be wirelessly connected with the external device 51 including an HR sensor and may obtain at least a part of HR data acquired by the external device 51, through the communication circuit 510 from the external device 51. In another example, the processor 550 may obtain HR data by using the HR sensor 520. The processor 550 may at least temporarily store information about at least a part of the HR data in the memory 540. The processor 550 may obtain an HR data sequence corresponding to the partial sequence of the contents, among the obtained HR data. For example, the processor 550 may obtain a sequence of HR data sensed for the period of time during which the captured partial sequence of the contents has been played back. In another example, the processor 550 may obtain a sequence of HR data sensed for the period of time included in the time data that corresponds to the partial sequence of the contents. The processor 550 may transmit the information stored in the memory 540 to the server 53 through the communication circuit 510. For example, the processor 550 may transmit the HR data sequence to the server 53 through the communication circuit 510.

According to an embodiment, the processor 550 may determine whether the HR data sequence satisfies a specified condition. For example, the processor 550 may determine whether emotion of the user of the electronic device 500 has changed, based on the HR data sequence. According to an embodiment, the processor 550 may perform a frequency analysis on the HR data sequence and may determine whether the HR data sequence satisfies the specified condition, based on an execution result of the frequency analysis. The processor 550 may perform the frequency analysis on the HR data sequence by using a technique, such as a Fourier Transform or a Fast Fourier Transform. For example, the processor 550 may determine whether a ratio of a power spectrum of the HR data sequence in a frequency band lower than a specified frequency to a power spectrum of the HR data sequence in a frequency band higher than the specified frequency satisfies the specified condition.

According to an embodiment, if the HR data sequence satisfies the specified condition, the processor 550 may store, in the memory 540, the portion of the media data that corresponds to the HR data sequence. The processor 550 may transmit the portion of the media data, which corresponds to the HR data sequence satisfying the specified condition, to the server 53 through the communication circuit 510.

According to an embodiment, the processor 550 may obtain emotional information of the user of the electronic device 500 on the basis of the HR data sequence that satisfies the specified condition. According to an embodiment, the processor 550 may obtain environmental information that includes at least some of first information obtained by the environmental sensor 530, second information about an application executed by the processor 550, and third information about the external device 51 connected through the communication circuit 510, and may obtain the emotional information on the basis of the HR data sequence and the environmental information. The processor 550 may tag the partial sequence of the contents, which corresponds to the HR data sequence, with the emotional information. The processor 550 may tag the portion of the media data, which corresponds to the HR data sequence, with the environmental information.

At least some of the operations described herein as being performed by the processor 550 of the electronic device 500 may also be performed by the external device 51 or the server 53. For example, the electronic device 500 may transmit the HR data to the server 53, and the server 53 may obtain emotional information on the basis of the transmitted HR data. In this case, the server 53 may transmit the obtained emotional information to the electronic device 500.

Figure 6:
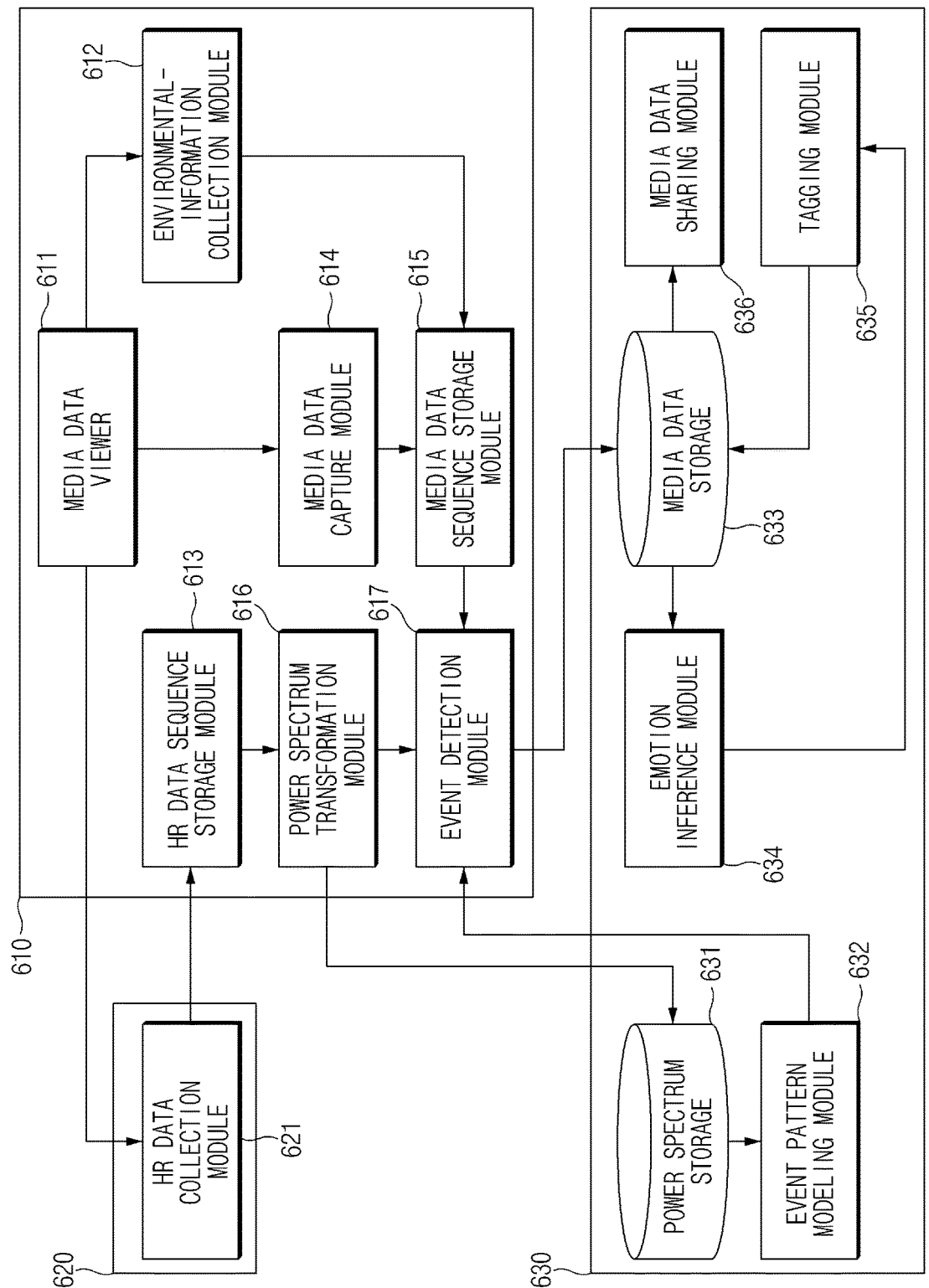
FIG. 6 is a block diagram of a program module stored in an electronic device, according to an embodiment.

FIG. 6 is a block diagram of a program module stored in an electronic device, according to an embodiment.

The program module illustrated in FIG. 6 may be executed by the electronic device 500, the external device 51, or the server 53 illustrated in FIG. 5. At least a part of the program module illustrated in FIG. 6 may be executed by the processor 550 of the electronic device 500 illustrated in FIG. 5. At least a part of a program module or storage illustrated as being included in an external device 620 or a server 630 in FIG. 6 may be included in an electronic device 610 according to an implemented embodiment of the present disclosure.

Referring to FIG. 6, a media data viewer 611 according to an embodiment may display a video, a photo, a web page, or output an audio signal, or the like. The media data viewer 611 may include, for example, a video player, a photo viewer, a music player, a web browser, or the like.

According to an embodiment, an environmental-information collection module 612 may collect information about surroundings of a user of the electronic device 610 while media data is output by the media data viewer 611. The environmental-information collection module 612 may collect the environmental information by using an environmental sensor (e.g., a microphone, a camera, a gyro sensor, an illuminance sensor, a GPS module, or the like).

According to an embodiment, an HR data collection module 621 may collect HR data of the user of the electronic device 610 while the media data is output by the media data viewer 611. The HR data collection module 621 may collect the HR data by using an HR sensor of the external device 620. While FIG. 6 illustrates that the HR data collection module 621 is included in the external device 620, the HR data collection module 621 may be included in the electronic device 610 and may collect the HR data by using an HR sensor included in the electronic device 610.

According to an embodiment, while the contents are being output by the media data viewer 611, a media data capture module 614 may generate snapshots of the media data being output. The snapshots may include an image and sound. The media data capture module 614 may store the snapshots and time data corresponding to the snapshots.

According to an embodiment, a media data storage module 615 may store the snapshots in a chronological order. For example, the media data storage module 615 may store a specified number of snapshots in a chronological order by using a sliding window. The sliding window may perform a function of storing data in a chronological order. If new data is input to the sliding window, the oldest data in the sliding window may be deleted. The media data module 615 may store the specified number of snapshots in a first-in-first-out (FIFO) manner. In certain embodiments, the media data module 615 can use a circular buffer.

According to an embodiment, an HR data sequence storage module 613 may store the HR data in a chronological order. For example, the HR data sequence storage module 613 may store a sequence of a specified number of HR data in a chronological order by using a sliding window. The specified number associated with the HR data may be different from the specified number associated with the media data. The HR data sequence storage module 613 may store the specified number of HR data sequence in a FIFO manner. In certain embodiments, the storage module 613 can use a circular buffer. The period of time during which the portion of the media data stored by the media data storage module 615 has been displayed may synchronize with the period of time during which the HR data sequence stored by the HR data sequence storage module 613 has been obtained.

According to an embodiment, a power spectrum transformation module 616 may perform a Fourier Transform on the HR data sequence, which is stored by the HR data sequence storage module 613, to obtain a power spectrum of the HR data sequence. The power spectrum transformation module 616 may randomly select at least some of the HR data included in the HR data sequence and may perform a Fast Fourier Transform on the selected HR data. The power spectrum transformation module 616 may calculate a ratio (LF/HF) of a power spectrum in a low-frequency (LF) band (e.g., 0.04 Hz to 0.15 Hz) to a power spectrum in a high-frequency (HF) band (e.g., 0.15 Hz to 0.4 Hz). The power spectrum transformation module 616 may transmit the LF/HF to power spectrum storage 631.

According to an embodiment, the power spectrum storage 631 may store the LF/HF. The power spectrum storage 631 may store the received LF/HF in a chronological order. The power spectrum storage 631 may consistently store the received LF/HF and may retain a plurality of LF/HF values.

According to an embodiment, an event pattern modeling module 632 may analyze the LF/HF values stored in the power spectrum storage 631 to distinguish between a general sequence of LF/HF values and an event sequence of LF/HF values. For example, the event pattern modeling module 632 may analyze a variation pattern of the plurality of LF/HF values stored in the power spectrum storage 631 to distinguish between an LF/HF sequence within a typical variation range and an LF/HF sequence outside the typical variation range. The event pattern modeling module 632 may generate reference data (an event sequence) for determining whether an event occurs or not, based on the plurality of LF/HF values.

According to an embodiment, an event detection module 617 may determine whether an event occurs or not, based on the LF/HF sequence calculated by the power spectrum transformation module 616. For example, the event detection module 617 may compare the LF/HF sequence calculated by the power spectrum transformation module 616 and the event sequence distinguished by the event pattern modeling module 632. In the case where a sub-sequence similar to the event sequence is included in the LF/HF sequence, the event detection module 617 may determine that an event has occurred in the corresponding LF/HF sequence. The occurrence of the event may correspond to a change in the user's emotion. The event detection module 617 may transmit, to media data storage 633, the LF/HF sequence, on the basis of which it is determined that the event has occurred, and the portion of the media data corresponding to the LF/HF sequence. For example, the LF/HF sequence and the portion of the media data may have the same time data. The event detection module 617 may transmit environmental information corresponding to the portion of the media data to the media data storage 633.

According to an embodiment, the media data storage 633 may store the portion of the media data and the LF/HF sequence. The contents storage 633 may also store the environmental information corresponding to the portion of the media data. The media data storage 633 may store the received information in a chronological order.

According to an embodiment, an emotion inference module 634 may infer emotion of the user of the electronic device 610 on the basis of the LF/HF sequence and the environmental information. For example, the emotion inference module 634 may obtain emotional information, based on, for example, a method described in an article entitled, "Revealing Real-Time Emotional Responses: a Personalized Assessment based on Heartbeat Dynamics," by G. Valenza, L. Citi, A. Lanata, E. P. Scilingo, and R. Barbieri (Scientific Reports 4, Article number: 4998, 2014), which is incorporated herein by reference.

According to an embodiment, a tagging module 635 may tag the emotional-information-related contents sequence with the emotional information. The tagging module 635 may modify the emotional information in response to the user's request.

According to an embodiment, a media data sharing module 636 may share the portion of the media data stored in the media data storage 633 with another user. The media data sharing module 636 may share the contents sequence tagged with the emotional information.

Figure 7:
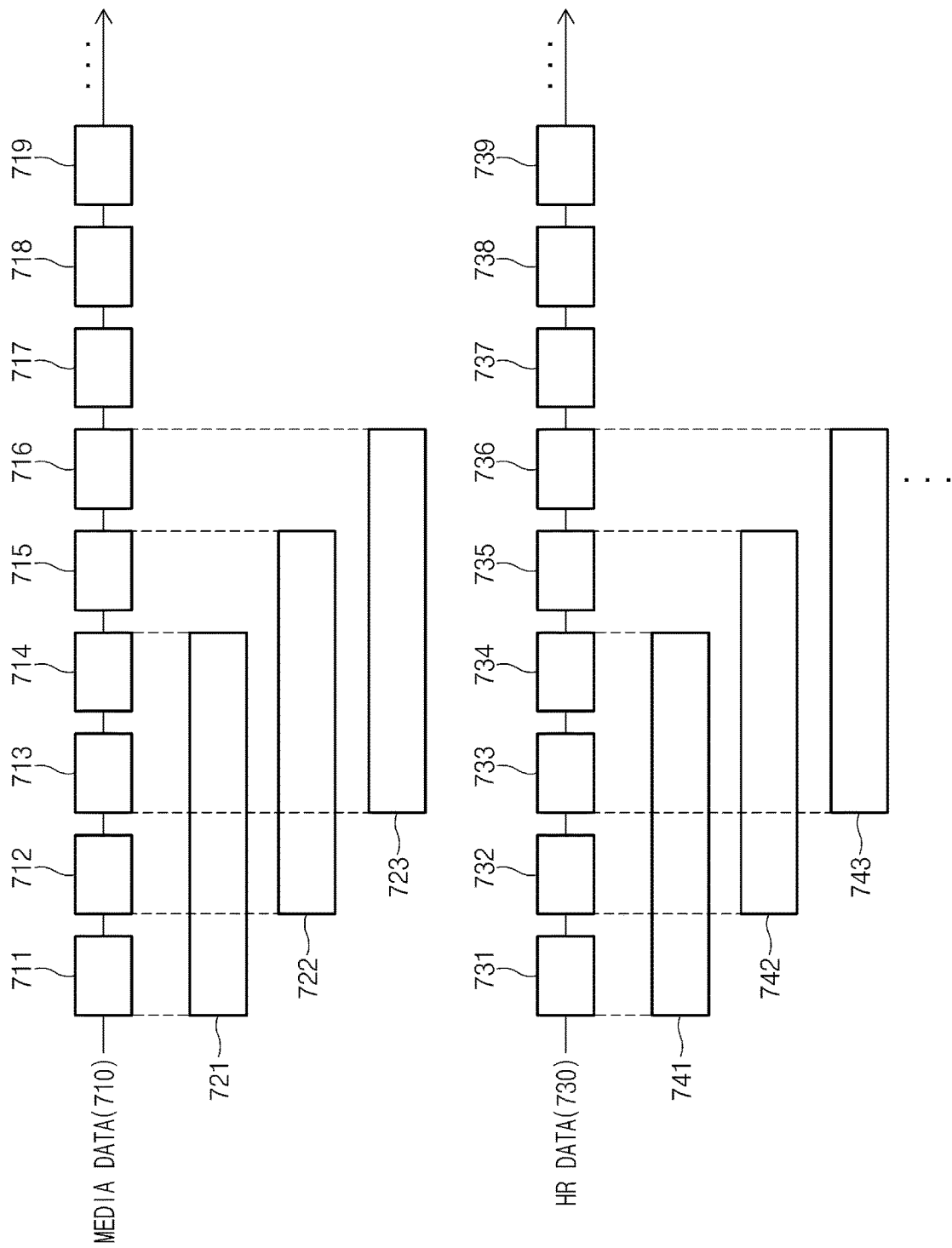
FIG. 7 is a diagram for explaining a method of storing contents and HR data in an electronic device, according to an embodiment.

FIG. 7 is a diagram for explaining a method of storing media data and HR data in an electronic device, according to an embodiment.

It may be understood that operations described as being performed by the electronic device in the description of FIG. 7 are controlled by the processor 550 of the electronic device 500.

According to an embodiment, while media data is output, the electronic device may obtain a portion of the media data and a sequence of HR data by using a sliding window.

Referring to FIG. 7, the electronic device according to an embodiment may play back media data 710. While the media data 710 are being played back, the electronic device may obtain, for example, snapshots 711 to 719 of the media data 710. The snapshots 711 to 719 may be frames included in the media data 710. While the media data 710 are being played back, the electronic device may obtain HR data 730. The electronic device may obtain the HR data 730 that includes, for example, first to ninth data 731 to 739.

According to an embodiment, if the media data 710 are played back to a section including the fourth snapshot 714, the electronic device may obtain a first portion of the media data 721 containing the first to fourth snapshots 711 to 714, by using a sliding window. The electronic device may obtain a first HR data sequence 741 acquired for the duration of playing back the first portion of the media data 721, by using the sliding window. The first HR data sequence 741 may contain the first to fourth data 731 to 734.

According to an embodiment, if the media data 710 are played back to a section including the fifth snapshot 715, the electronic device may obtain a second contents sequence 722 containing the second to fifth snapshots 712 to 715, by using the sliding window. The electronic device may obtain a second HR data sequence 742 acquired for the duration of playing back the second portion of the media data 722, by using the sliding window. The second HR data sequence 742 may contain the second to fifth data 732 to 735.

According to an embodiment, if the contents 710 are played back to a section including the sixth snapshot 716, the electronic device may obtain a third contents sequence 723 containing the third to sixth snapshots 713 to 716, by using the sliding window. The electronic device may obtain a third HR data sequence 743 acquired for the duration of playing back the third portion of the media data 723, by using the sliding window. The third HR data sequence 743 may contain the third to sixth data 733 to 736.

As described above, the electronic device according to an embodiment may sequentially obtain the contents sequences and the HR data sequences while the media data 710 are being played back.

In FIG. 7, each portion of the media is illustrated as containing four snapshots, and each HR data sequence is illustrated as containing four data points. In certain embodiments, the HR data can be an instantaneous number of heart beats/second at the measured time. Without being limited thereto, however, each portion of the media data may contain various numbers of snapshots determined in advance, and each HR data sequence may contain various numbers of data points determined in advance. The number of snapshots contained in each contents sequence may be different from the number of data contained in each HR data sequence. However, the period of time corresponding to the contents sequence may be the same as the period of time corresponding to the HR data sequence.

Figure 8:
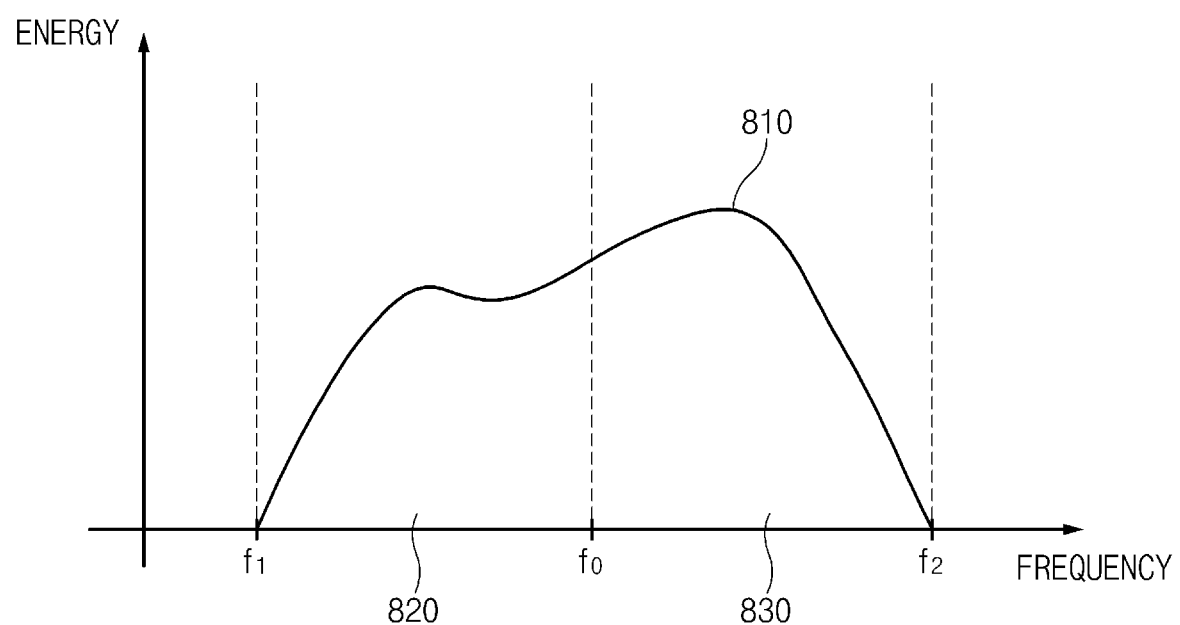
FIG. 8 is a graph illustrating energy versus frequency for a sequence of HR data obtained by an electronic device, according to an embodiment.

FIG. 8 is a graph illustrating energy versus frequency for a sequence of HR data obtained by an electronic device, according to an embodiment.

It may be understood that operations described as being performed by the electronic device in the description of FIG. 8 are controlled by the processor 550 of the electronic device 500.

According to an embodiment, based on an execution result of a frequency analysis, the electronic device may determine whether a ratio of a component of an HR data sequence in a second frequency band to a component of the HR data sequence in a first frequency band satisfies a specified condition.

Referring to FIG. 8, the electronic device according to an embodiment may perform a Fourier Transform on an HR data sequence. In certain embodiments, the HR sequence can be the number of heart beats per second at given times. The electronic device may obtain a curve 810 showing a relation between energy and frequency for the HR data sequence, by performing the Fourier Transform. The electronic device may calculate the area of a first region 820 between a reference frequency $f_0$ (e.g., about 0.15 Hz) and a first frequency $f_1$ (e.g., about 0.04 Hz). The electronic device may calculate the area of a second region 830 between the reference frequency $f_0$ and a second frequency $f_2$ (e.g., about 0.4 Hz). The electronic device may obtain LF/HF by calculating a ratio of the area of the first region 820 to the area of the second region 830.

Figure 9:
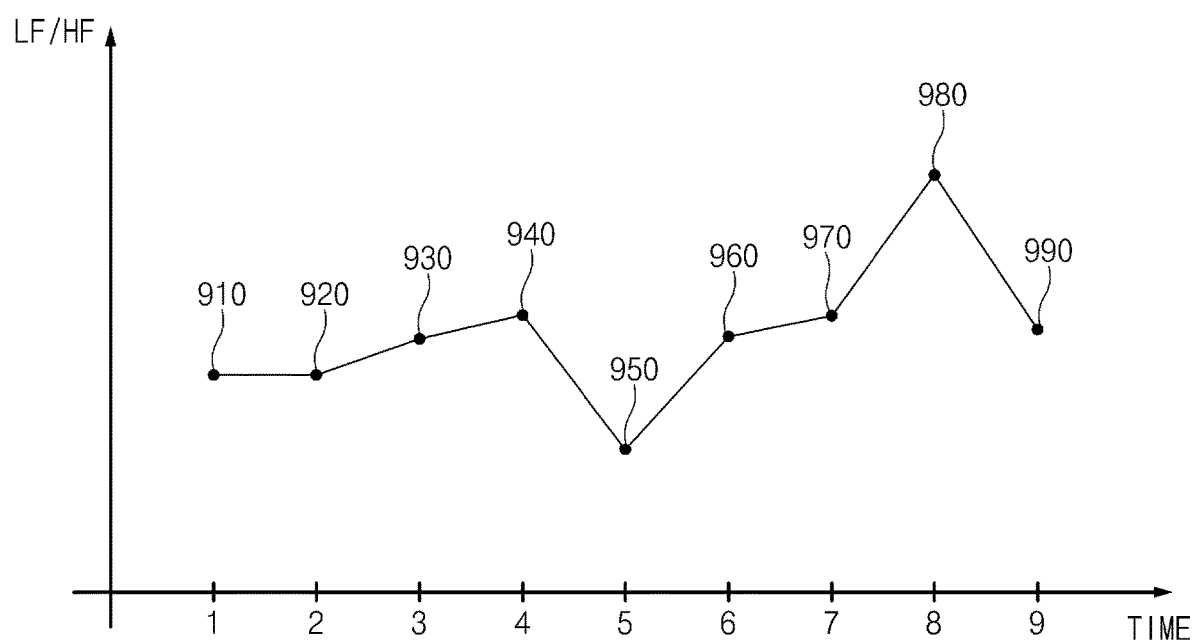
FIG. 9 is a graph illustrating LF/HF values according to time, which are obtained by an electronic device, according to an embodiment.

FIG. 9 is a graph illustrating LF/HF values according to time, which are obtained by an electronic device, according to an embodiment.

It may be understood that operations described as being performed by the electronic device in the description of FIG. 9 are controlled by the processor 550 of the electronic device 500.

According to an embodiment, the electronic device may determine whether a ratio of a component in a second frequency band to a component in a first frequency band, among a sequence of HR data, satisfies a specified condition, by comparing the ratio of the component in the second frequency band to the component in the first frequency band, among the HR data sequence, and a ratio of a component in the second frequency band to a component in the first frequency band, among a sequence of HR data that corresponds to another partial sequence of contents.

Referring to FIG. 9, the electronic device may obtain first to ninth LF/HF values 910 to 990. The first to ninth LF/HF values 910 to 990 may correspond to first to ninth HR data sequences, respectively. The electronic device may sequentially obtain the first to ninth LF/HF values 910 to 990. The electronic device may determine a change in emotion of a user of the electronic device, based on at least some of the first to ninth LF/HF values 910 to 990. For example, if there is a large difference between the LF/HF values, the electronic device may determine that a specified condition is satisfied.

For example, based on the first to fourth LF/HF values 910 to 940, the electronic device may determine whether emotion of the user of the electronic device has changed for the duration of playing back a contents sequence corresponding to the fifth LF/HF value 950. Since the fifth LF/HF value 950 is remarkably lower than the first to fourth LF/HF values 910 to 940, the electronic device may determine that the emotion of the user of the electronic device has changed for the duration of playing back the contents sequence corresponding to the fifth LF/HF value 950.

In another example, based on the first to seventh LF/HF values 910 to 970, the electronic device may determine whether emotion of the user of the electronic device has changed for the duration of playing back a contents sequence corresponding to the eighth LF/HF value 980. Since the eighth LF/HF value 980 is remarkably higher than the first to seventh LF/HF values 910 to 970, the electronic device may determine that the emotion of the user of the electronic device has changed for the duration of playing back the contents sequence corresponding to the eighth LF/HF value 980.

The electronic device may obtain emotional information of the user of the electronic device, based on the first to ninth LF/HF values 910 to 990.

Figure 10:
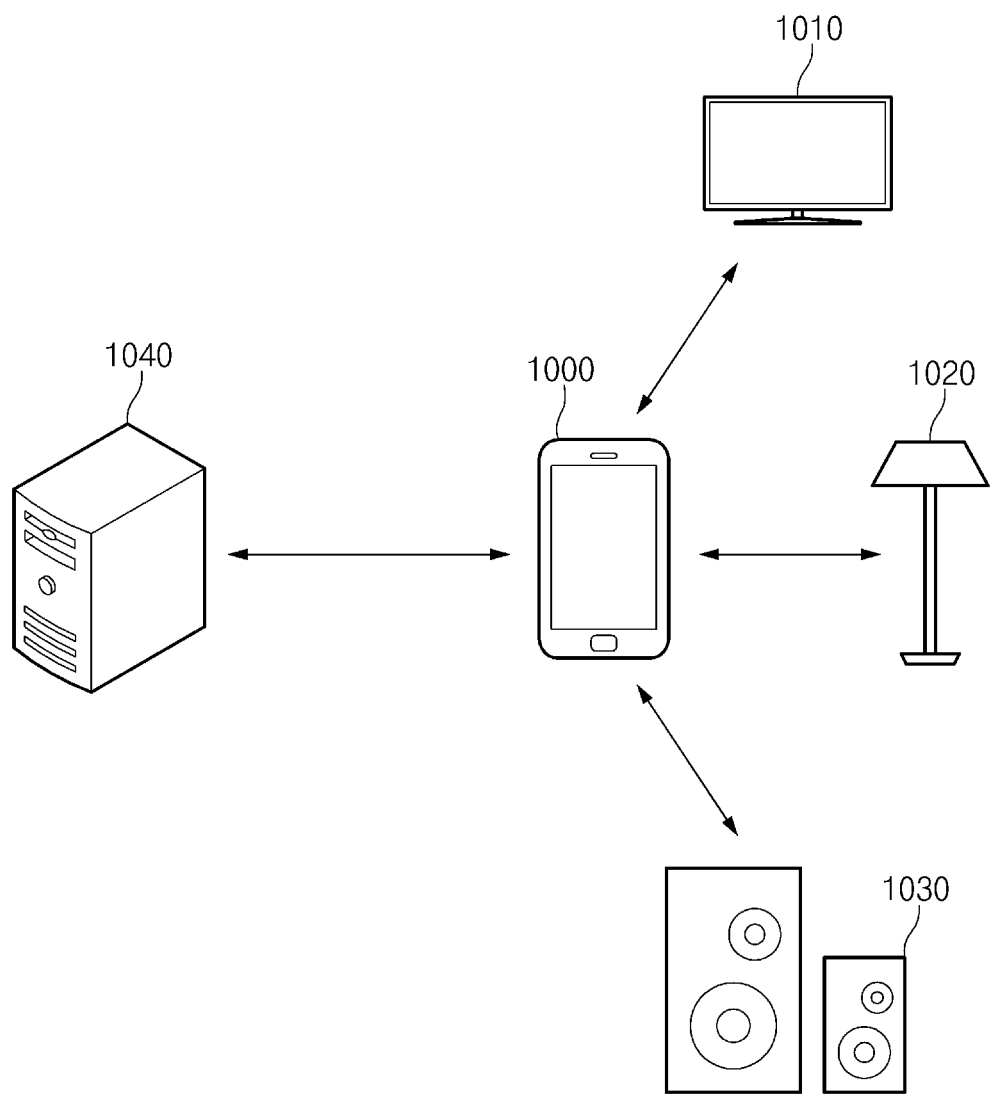
FIG. 10 illustrates an electronic device, according to an embodiment, which is connected with various external devices.

FIG. 10 illustrates an electronic device, according to an embodiment, which is connected with various external devices.

Referring to FIG. 10, an electronic device 1000 according to an embodiment may support Internet of Things (IoT). The electronic device 1000 may operate in conjunction with various home appliances, such as TV 1010, a lighting device 1020, a speaker 1030, and the like. The electronic device 1000 may communicate with a server 1040 for providing a contents service. The server 1040 may provide, for example, a audio data.

According to an embodiment, the electronic device 1000 may provide, to the server 1040, information about a portion of the audio data in which a change in emotion of a user of the electronic device 1000 is detected while a audio data is output. In certain embodiments, the information about the portion of the audio data can include a time period according to the time base of the audio data. For example, the electronic device 1000 may provide, to the server 1040, a portion of the audio data corresponding to HR data that satisfies a specified condition. The electronic device 1000 may provide, to the server 1040, emotional information obtained while the sound source is being played back. The electronic device 1000 may provide, to the server 1040, information about the user of the electronic device 1000 (e.g., the user's age and gender).

According to an embodiment, the server 1040 may create a personalized profile on the basis of the information received from the electronic device 1000. The server 1040 may provide a variety of services to the electronic device 1000 by using the personalized profile. For example, the server 1040 may store the portion of the audio data received from the electronic device 1000 and may provide the stored portion of the audio data to the electronic device 1000. In another example, the server 1040 may recommend other audio data associated with the user's affirmative emotional information to the electronic device 1000. In the case where affirmative emotional information of the user of the electronic device 1000 is obtained while classical music is being played back in the electronic device 1000, the server 1040 may recommend classical music to the electronic device 1000. In another example, the server 1040 may recommend a audio data to the electronic device 1000 on the basis of emotional information collected from a plurality of devices and user information. The server 1040 may obtain, for example, information that a plurality of male users in their 30s prefer rock music, by analyzing the emotional information and the user information, and in the case where the user of the electronic device 1000 is a male in his thirties, the server 1040 may recommend audio data having rock music to the electronic device 1000. The server 1040 may provide a variety of services to the electronic device 1000 on the basis of the information collected from the electronic device 1000.

According to an embodiment, while audio data is being played back, the electronic device 1000 may obtain information about various home appliances, such as the TV 1010, the lighting device 1020, the speaker 1030, and the like, as context information. For example, the electronic device 1000 may obtain information about the channel, volume, or brightness of the TV 1010, information about the color or brightness of the lighting device 1020, and information about the tone or volume of the speaker 1030. The electronic device 1000 may store the context information and may transmit the context information to the server 1040. The server 1040 may store the context information. In the case where the sound source associated with the context information is played back again, the electronic device 1000 may control the TV 1010, the lighting device 1020, and the speaker 1030 on the basis of the context information provided from the server 1040 or stored in the electronic device 1000. In another example, the electronic device 1000 may control the TV 1010, the lighting device 1020, and the speaker 1030 on the basis of context information collected while a sound source sequence satisfying a specified condition is being played back. In another example, the electronic device 1000 may control the TV 1010, the lighting device 1020, and the speaker 1030 on the basis of context information collected for the period of time during which affirmative emotional information has been obtained.

Figure 11:
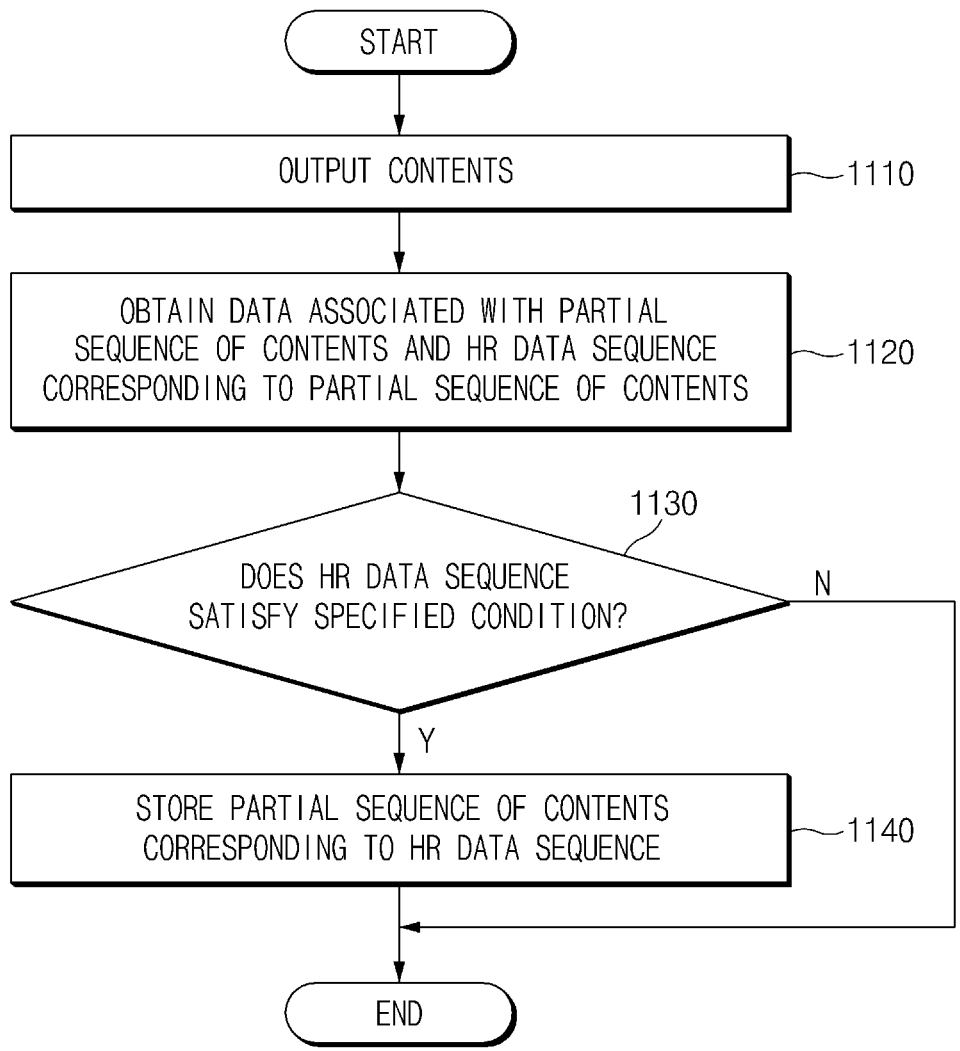
FIG. 11 is a flowchart illustrating a method for capturing contents in an electronic device, according to an embodiment.

FIG. 11 is a flowchart illustrating a method for capturing contents in an electronic device, according to an embodiment.

Hereinafter, it is assumed that the electronic device 500 of FIG. 5 performs the process illustrated in FIG. 11. Furthermore, it may be understood that operations described as being performed by the electronic device in the description of FIG. 11 are controlled by the processor 550 of the electronic device 500.

Referring to FIG. 11, in operation 1110, the electronic device according to an embodiment may output media data. For example, the electronic device may output a photo, video data, a audio data, a web page, or the like, by using a display and/or a speaker.

In operation 1120, the electronic device according to an embodiment may obtain identification of a portion of the media data and an HR data sequence corresponding to the partial sequence of the contents. For example, the electronic device may obtain the portion of the media data using a sliding window. The electronic device may also obtain time data corresponding to the portion of the media data. The electronic device may obtain a sequence of HR data collected for the period of time during which the portion of the media data has been played back or for the period of time corresponding to the time data.

In operation 1130, the electronic device according to an embodiment may determine whether the HR data sequence satisfies a specified condition. For example, the electronic device may determine whether a ratio between energy of the HR data sequence in a first frequency band and energy of the HR data sequence in a second frequency band satisfies the specified condition.

If the specified condition is satisfied, the electronic device according to an embodiment may, in operation 1140, store the portion of the media data that corresponds to the HR data sequence. For example, the electronic device may store the portion of the media data was output for the period of time during which the HR data sequence satisfying the specified condition has been obtained. The electronic device may provide the stored portion of the media data to a user.

Figure 12:
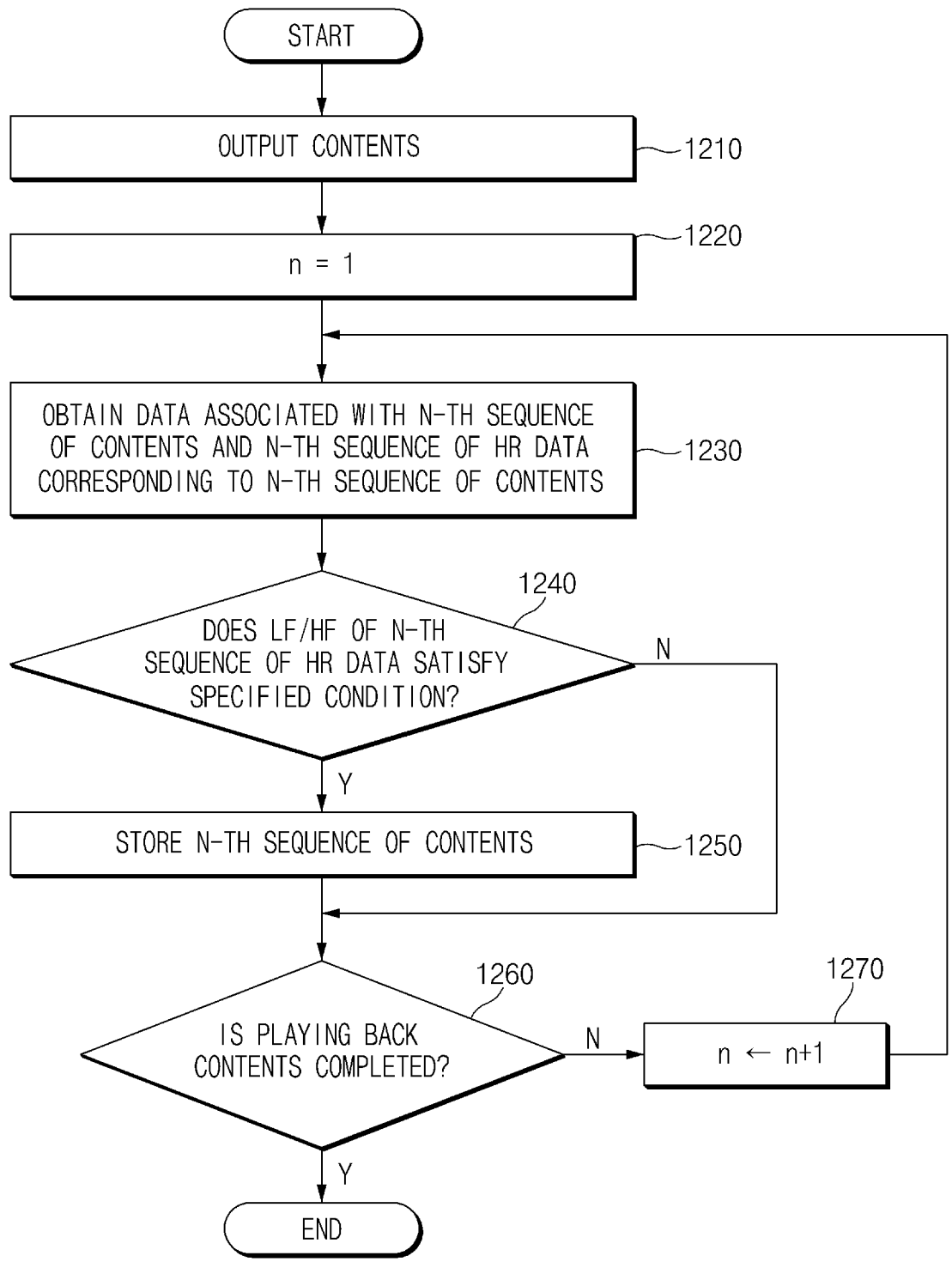
FIG. 12 is a flowchart illustrating a method for capturing contents in an electronic device, according to an embodiment.

FIG. 12 is a flowchart illustrating a method for capturing media data in an electronic device, according to an embodiment.

Hereinafter, it is assumed that the electronic device 500 of FIG. 5 performs the process illustrated in FIG. 12. Furthermore, it may be understood that operations described as being performed by the electronic device in the description of FIG. 12 are controlled by the processor 550 of the electronic device 500. Repetitive description of the operations described with reference to FIG. 11 will be omitted for the convenience of description.

Referring to FIG. 12, in operation 1210, the electronic device according to an embodiment may output media data.

In operation 1220, the electronic device according to an embodiment may set n to 1. For example, the electronic device may perform the following operations 1230 to 1260 on a first sequence of the contents. The first sequence of the contents may contain first to k-th frames of the media data. For example, where the media data is video, the first to kth frames may be video frames.

In operation 1230, the electronic device according to an embodiment may obtain data associated with the first portion of the media data and a first sequence of HR data that corresponds to the first portion of the media data.

In operation 1240, the electronic device according to an embodiment may determine whether LF/HF of the first sequence of the HR data satisfies a specified condition. For example, the electronic device may perform a Fourier Transform on the first sequence of the HR data to calculate a ratio of a power spectrum in a low-frequency band to a power spectrum in a high-frequency band. The electronic device may determine, for example, whether the LF/HF is included in a specified range, or whether a variation pattern of the LF/HF is similar to a specified pattern.

If the specified condition is satisfied, the electronic device according to an embodiment may, in operation 1250, store the first portion of the media data.

In operation 1260, the electronic device according to an embodiment may determine whether playing back the media data is completed. For example, the electronic device may repeat operations 1230 to 1260 until completion of playing back the media data, and may end the operations if playing back the contents is completed.

In the case where playing back the media is not completed, the electronic device according to an embodiment may, in operation 1270, set n to 2. The electronic device may perform operations 1230 to 1250 again on a second sequence of the contents. The second sequence may contain second to (k+1)th frames of the contents.

The electronic device may repeatedly perform operations 1230 to 1250 on the next sequences until playing back the media data is completed. The electronic device may end the operations if playing back the media data is completed.

The term "module" used in this disclosure may include a unit composed of hardware, software and firmware and may be interchangeably used with the terms "unit", "logic", "logical block", "component" and "circuit". The "module" may be an integrated component or may be a minimum unit for performing one or more functions or a part thereof. The "module" may be implemented mechanically or electronically and may include at least one of an application-specific IC (ASIC) chip, a field-programmable gate array (FPGA), and a programmable-logic device for performing some operations, which are known or will be developed. At least a part of an apparatus (e.g., modules or functions thereof) or a method (e.g., operations) according to various embodiments may be, for example, implemented by commands (or instructions) stored in computer-readable storage media (e.g., the memory 130) in the form of a program module. The instruction, when executed by a processor (e.g., the processor 120), may cause the processor to perform a function corresponding to the instruction. A computer-readable recording medium may include a hard disk, a floppy disk, a magnetic media (e.g., a magnetic tape), an optical media (e.g., a compact disc read only memory (CD-ROM) and a digital versatile disc (DVD), a magneto-optical media (e.g., a floptical disk)), and an internal memory. Also, a program instruction may include not only a mechanical code such as things generated by a compiler but also a high-level language code executable on a computer using an interpreter. A module or a program module according to various embodiments may include at least one of the above elements, or a part of the above elements may be omitted, or other elements may be further included. Operations performed by a module, a program module, or other elements according to various embodiments may be executed sequentially, in parallel, repeatedly, or in a heuristic method or some operations may be executed in different sequences or may be omitted. Alternatively, other operations may be added.

While the present disclosure has been shown and described with reference to various embodiments thereof, it will be understood by those skilled in the art that various changes in form and details may be made therein without departing from the spirit and scope of the present disclosure as defined by the appended claims and their equivalents.

What is claimed is:

1. An electronic device comprising:
   a display;
   a media data storage; and
   a processor electrically connected with the media data storage and the display, wherein the processor is configured to:
output media data on the display,
capture a plurality of snapshots of the output media data while outputting the media data,
obtain a sequence of heart rate (HR) data of a user of the electronic device while outputting the media data,
store the plurality of snapshots to a first buffer in a FIFO (first-in first-out) manner, the first buffer being configured to store a first number of snapshots,
store the sequence of HR data to a second buffer in the FIFO manner, the second buffer being configured to store a second number of HR data,
determine whether HR data stored in the second buffer corresponds to a particular emotion,
when the HR data corresponds to the particular emotion, store the first number of snapshots of the first buffer in the media data storage, and
wherein the first buffer and the second buffer are synchronized in a time domain.

2. The electronic device of claim 1, further comprising:
a communication circuit configured to communicate with an external device,
wherein the processor is configured to obtain the sequence of HR data from the external device using the communication circuit.

3. The electronic device of claim 1, further comprising:
a HR sensor configured to sense a heart rate (HR) of the user of the electronic device,
wherein the processor is configured to obtain the sequence of HR data using the HR sensor.

4. The electronic device of claim 1, wherein the processor is configured to:
perform a frequency analysis on the HR data stored in the second buffer; and
determine whether the HR data corresponds to the particular emotion, based on a result of the frequency analysis.

5. The electronic device of claim 4, wherein the processor is configured to determine whether a ratio of a component in a second frequency band to a component in a first frequency band, among the HR data, corresponds to the particular emotion, based on the result of the frequency analysis.

6. The electronic device of claim 1, further comprising:
a communication circuit configured to communicate with a server,
wherein the processor is configured to transmit the HR data to the server using the communication circuit.

7. The electronic device of claim 1, further comprising:
a communication circuit configured to communicate with a server,
wherein the processor is configured to transmit, to the server, the first number of snapshots of the first buffer when the HR data corresponds to the particular emotion.

8. The electronic device of claim 1, wherein the processor is configured to tag the first number of the snapshots stored in the media data storage with emotional information.

9. The electronic device of claim 1, further comprising:
a communication circuit configured to communicate with an external device; and
an environmental sensor including at least part of a microphone, a camera, a gyro sensor, an illuminance sensor, or a GPS module,
wherein the processor is configured to:
obtain environmental information that includes first information obtained by the environmental sensor, second information about an application executed by the processor, and third information about the external device connected through the communication circuit; and
obtain emotional information based on the HR data and the environmental information.

10. The electronic device of claim 9, wherein the processor is configured to tag the first number of the snapshots stored in the media data storage with the environmental information.

11. A method for extracting a portion of media data in an electronic device, the method comprising:
outputting the media data;
capturing a plurality of snapshots of the output media data while outputting the media data;
obtaining a sequence of heart rate (HR) data of a user of the electronic device while outputting the media data;
storing the plurality of snapshots to a first buffer in a FIFO (first-in first-out) manner, the first buffer being configured to store a first number of snapshots; and
storing the sequence of HR data to a second buffer in the FIFO manner, the second buffer being configured to store a second number of HR data,
wherein the method further comprises:
determining whether HR data stored in the second buffer corresponds to a particular emotion;
when the HR data corresponds to the particular emotion, store the first number of snapshots of the first buffer, and
wherein the first buffer and the second buffer are synchronized in a time domain.

12. The method of claim 11, further comprising:
determining whether the HR data corresponds to the particular emotion, based on a ratio of a component of the HR data in a second frequency band to a component of the HR data in a first frequency band.

* * * * *